(12) United States Patent
Rosichan

(10) Patent No.: US 9,212,373 B2
(45) Date of Patent: Dec. 15, 2015

(54) CONTROL OF TARGETED TURNOVER OF KEY ETHYLENE HORMONE SIGNALING PATHWAY PROTEINS TO MODULATE ETHYLENE SENSITIVITY IN PLANTS

(75) Inventor: Jeffrey L. Rosichan, Ambler, PA (US)

(73) Assignee: AgroFresh Inc., Collegeville, PA (US)

( * ) Notice: Subject to any disclaimer, the term of this patent is extended or adjusted under 35 U.S.C. 154(b) by 1069 days.

(21) Appl. No.: 13/254,937

(22) PCT Filed: Mar. 2, 2010

(86) PCT No.: PCT/US2010/025872
§ 371 (c)(1),
(2), (4) Date: Sep. 6, 2011

(87) PCT Pub. No.: WO2010/101884
PCT Pub. Date: Sep. 10, 2010

(65) Prior Publication Data
US 2011/0321191 A1    Dec. 29, 2011

Related U.S. Application Data

(60) Provisional application No. 61/157,759, filed on Mar. 5, 2009.

(51) Int. Cl.
*C12N 15/82* (2006.01)

(52) U.S. Cl.
CPC ........ *C12N 15/8291* (2013.01); *C12N 15/8216* (2013.01); *C12N 15/8217* (2013.01); *C12N 15/8238* (2013.01); *C12N 15/8249* (2013.01); *C12N 15/8261* (2013.01); *C12N 15/8266* (2013.01); *C12N 15/8267* (2013.01)

(58) Field of Classification Search
None
See application file for complete search history.

(56) References Cited

U.S. PATENT DOCUMENTS

| 5,880,333 | A | 3/1999 | Goff et al. | |
|---|---|---|---|---|
| 6,245,531 | B1 | 6/2001 | Hogness et al. | |
| 6,258,603 | B1 | 7/2001 | Carlson et al. | |
| 6,265,173 | B1 | 7/2001 | Evans et al. | |
| 6,294,716 | B1 | 9/2001 | Meyerowitz et al. | |
| 6,333,318 | B1 | 12/2001 | Evans et al. | |
| 6,784,340 | B1 * | 8/2004 | Aoyama et al. | 800/290 |
| 7,091,038 | B2 | 8/2006 | Palli et al. | |
| 7,456,315 | B2 * | 11/2008 | Hormann et al. | 564/148 |
| 8,115,059 | B1 * | 2/2012 | Palli et al. | 800/288 |
| 8,168,860 | B2 | 5/2012 | Rosichan | |
| 2003/0154509 | A1 | 8/2003 | Pascal et al. | |
| 2003/0188331 | A1 | 10/2003 | Choo et al. | |
| 2004/0128719 | A1 | 7/2004 | Klee et al. | |
| 2005/0060772 | A1 | 3/2005 | Ciardi et al. | |
| 2005/0066389 | A1 | 3/2005 | Gallie et al. | |
| 2005/0266457 | A1 | 12/2005 | Palli et al. | |
| 2006/0200875 | A1 | 9/2006 | Guo et al. | |
| 2008/0235816 | A1 | 9/2008 | Dhadialla et al. | |
| 2009/0077684 | A1 | 3/2009 | Gallie et al. | |

FOREIGN PATENT DOCUMENTS

| WO | WO 97/38117 | 10/1997 |
|---|---|---|
| WO | WO 01/34821 | 5/2001 |
| WO | WO 03/088738 | 10/2003 |
| WO | WO 2009/039001 | 3/2009 |

OTHER PUBLICATIONS

Qiao et al, Genes & Development, published online Feb. 12, 2008 (cited in the IDS filed Nov. 16, 2011).*
Czarny et al, Biotechnology Advances, Jul. 1, 2006, vol. 24, pp. 410-419 (cited in the IDS filed Aug. 28, 2014).*
Gallie, Regulated ethylene insensitivity through the inducible expression of the Arabidopsis etr1-1 mutant ethylene receptor in tomato, Plant Physiol., Feb. 24, 2010, vol. 152(4):1928-1934.
Czarny, "Genetic modulation of ethylene biosynthesis and signaling in plants", Biotech Adv., Jul. 1, 2006 vol. 24:410-419.
Reply to Examination Report of Jul. 23, 2012 in corresponding EP Application No. 10749182.1, dated Nov. 16, 2012.
Examination Report dated Jun. 7, 2013 in corresponding EP Application No. 10749182.1.
Reply to Examination Report of Jun. 7, 2013 in corresponding EP Application No. 10749182.1, dated Oct. 8, 2013.

(Continued)

*Primary Examiner* — Eileen B O Hara
(74) *Attorney, Agent, or Firm* — Howson & Howson LLP

(57) ABSTRACT

A gene expression system for controllable expression of ethylene response in a plant cell includes an activation cassette comprising a DNA-binding domain that recognizes a response element; an ecdysone receptor ligand binding domain; and an activation domain; and a target cassette comprising an inducible promoter, which comprises, in operative association, the response element and a minimal promoter responsive to the activation domain. The inducible promoter controls the expression of a nucleic acid sequence that encodes a selected regulatory protein that modifies sensitivity to ethylene of certain signal proteins in the plant. Interaction among the components of the activation cassette and target cassette, when in a plant cell, in the presence of an inducing composition, increases expression of the selected regulatory protein, and in turn decreases expression and accumulation of the signal protein in the plant, thereby and decreasing ethylene sensitivity in the plant cell. This increase in the expression of the regulatory protein, particularly in the presence of ethylene, is controlled by the timing, the concentration and the duration of the application of the inducing composition. Transgenic plant cells, tissues, organs and entire plants are provided, which in the presence of the inducing composition control ethylene sensitivity. Ethylene sensitivity and/or ethylene production in such transgenic plants and tissues may be controlled for purposes of manipulating ripening, flower senescence and other ethylene sensitive functions of the plant.

11 Claims, 20 Drawing Sheets

(56) References Cited

OTHER PUBLICATIONS

Examination Report dated Apr. 29, 2014 in corresponding EP Application No. 10749182.1.
Reply to Examination Report of Apr. 29, 2014 in corresponding EP Application No. 10749182.1, dated Aug. 5, 2014.
Reply to First Office Action of Jul. 16, 2012 in corresponding Chinese Application No. 201080010816.2, dated Nov. 13, 2012.
Second Office Action (translation) dated Mar. 18, 2013 in corresponding Chinese Application No. 201080010816.2.
Office Action (translation) dated May 16, 2014 in corresponding Mexican Application No. MX/a/2011/009239.
European Supplemental Search Report dated Jul. 9, 2010 in related EP Application No. 08831345.
Examination Report dated Jul. 27, 2010 in related EP Application No. 08831345.
Reply to Examination Report of Jul. 27, 2010 in related EP Application No. 08831345, dated May 20, 2011.
Examination Report dated Nov. 29, 2011 in related EP Application No. 08831345.
Reply to Examination Report of Nov. 29, 2011 in related EP Application No. 08831345, dated Mar. 28, 2012.
Examination Report dated Jul. 30, 2013 in related EP Application No. 08831345.
Reply to Examination Report of Jul. 30, 2013 in related EP Application No. 08831345, dated Nov. 12, 2013.
Invitation under EPC 94(3) and Rule 71(1) in related EP Application No. 08831345, dated Jun. 6, 2014.
Padidim, "Chemically regulated gene expression in plants," 2003 Curr. Opin Plant Biol., 6(2): 169-77.
Qiao, et al., "Interplay between ethylene, ETP1/ETP2 F-box proteins, and degradation of EIN2 triggers ethylene responses in Arabidopsis," Genes Dev., 23:000-000 Feb. 12, 2008.
Guo, "Plant Responses to Ethylene Gas Are Mediated by SCF EBF1/EBF2-Dependent Proteolysis of EIN3 Trnascription Factor," Cell, 115:667-677 Dec. 12, 2003.
Little, "Modified Ethylene Signaling as an Example of Engineering for Complex Traits: Secondary Effects and Implications for Environmental Risk," HortScience, 44(1): 94-101. 2009.
Gatz, Christine, "Chemically inducible promoters in transgenic plants", Current Opinion in Biotechnology, Apr. 1996, 7 (2): 168-172.
Aoyama, et al, "A glucocorticoid-mediated transcriptional induction system in transgenic plants", The Plant Journal, 1997, 11(3): 605-612.
Martinez, A. et al, "Ecdysone agonist inducible transcription in transgenic tobacco plants", The Plant Journal, Jul. 1999, 19(1):97-106.
Qiao, H. et al., "Interplay between ethylene, ETP1/ETP2 F-box proteins, and degradation of EIN2 triggers ethylene responses in Arabidopsis," Genes & Dev., Feb. 2009, 23(4):512-521.
Padidam, M. et al, "Chemical-inducible, ecdysone receptor-based gene expression system for plants", Transgenic Research, Jan. 2003, 12:101-109.
Wang, X. et al, "F-box proteins regulate ethylene signaling and more", Genes & Dev., Feb. 2009, 23(4):391-396.
Arora, A, et al, "Ethylene receptors and molecular mechanism of ethylene sensitivity in plants", Macromolecular: Rapid Communications, Oct. 2005, 89(8):1348-1361.
Zuo, et al. "An Estrogen receptor-based transactivator XVE mediates hightly inducible gene expression in transgenic plants", The Plant Journal, Aug. 2000, 24(2): 265-273.
Communication and Supplementary EP Search Report dated Jul. 5, 2012 issuing in corresponding EP Application No. 10749182.1.
Communication pursuant to Art 94(3) EPC dated Jul. 23, 2012 issuing in corresponding EP Application No. 10749182.1.
Office Action dated Jul. 16, 2012 issuing in corresponding Chinese Application No. 201080010816.2 with agent's English translation.
Office Action dated Oct. 29, 2010 in related U.S. Appl. No. 12/209,501, now U.S. Pat. No. 8,168,860 and Response filed on Mar. 29, 2011.
Office Action dated Jun. 7, 2011 in related U.S. Appl. No. 12/209,501, now U.S. Pat. No. 8,168,860 and Response filed on Sep. 7, 2011.
Office Action dated Nov. 8, 2011 in related U.S. Appl. No. 12/209,501, now U.S. Pat. No. 8,168,860 and Response filed on Feb. 8, 2012.
Sadowski, et at., "GAL4-VP16 is an unusually potent transcriptional activator", Nature., Oct. 1988, 335(6): 563-564.
Office Action dated Jan. 22, 2015 in corresponding Mexican Application No. MX/a/2011/009239 (original Spanish action and English translation).

* cited by examiner

Fig. 3B

```
                                                                  ATAGTT TAAACTGAAG GCGGGAAACG
                                                                                      G10-90 promoter
6301 ACAATCTGAT CCAAGCTCAA GCTAAGCTTG CATGCCTGCA GGATATCGTG GATCCAAGCT TGCCACGTGC CGCCACGTGC CGCCACGTGC
                   G10-90 promoter                                       G10-90 promoter
6401 CTCTAGAGGA TCCATCTCCA CTGACGTAAG GGATGACGCA CAATCCCACT ATCCTTCGCA AGACCCTTCC TCTATATAAG GAAGTTCATT TCATTTGGAG
        G10-90 promoter                                                                   VP16-Gal4
6501 AGGACACGCT GGGATCCCCA CCCGACCGAT GTCAGCCTGG GGGACGAACT CCACTTAGAC GGCGAGGACG TGGCGATGGC GCATGCCGAC
                                                           VP16-Gal4
6601 GCGCTAGACG ATTTCGATCT GGACATGTTG GGGGACGGGG ATTCCCCAGG TCCGGGATTT ACCCCCCACG ACTCCGCCCC CTACGGCGCT CTGGATATGG
                                                           VP16-Gal4
6701 CCGACTTCGA GTTTGAGCAG ATGTTTACCG AATTGACGAG TACGGTGGGA AGCTTCTAGG TACCTCCAGA AGAATATCAG GCGGGGAATT
                                                           VP16-Gal4
6801 CGGCGGGATG AAGCTACTGT CTTCTATCGA ACAAGCATGC GATATTTGCC GACTTAAAAA GCTCAAGTGC TCCAAAGAAA AACCGAAGTG CGCCAAGTGT
                                                           VP16-Gal4
6901 CTGAAGAACA ACTGGGAGTG TCGCTACTCT CCCAAAACCA AAAGGTCTCC GCTGACTAGG GCACATCTGA CAGAAGTGGA ATCAAGGCTA GAAAGACTGG
                                                           VP16-Gal4
7001 AACAGCTATT TCTACTGATT TTTCCTCGAG AAGACCTTGA CATGATTTTC AAAATGCATT CTTTACAGGA TATAAAAGCA TTGTTAACAG GATTATTTGT
                                                                                                    HpaI
7101 ACAAGATAAT GTGAATAAAG ATGCCGTCAC AGATAGATTG GCTTCAGTGG AGACTGATAT GCCTCTAACA TTGAGACAGC ATAGAATAAG TGCGACATCA
                                                           VP16-Gal4                                           EcR (wt)
7201 TCATCGGAAG AGAGTAGTAA CAAAGTCAA AGACAGTGA AGGCGGTGGG ATCCGGTGG AGTGCGTAGT ACCCGAGACT CAGTGCGCCA
                                                           EcR (wt)
```

Fig. 3C

```
7401 TGAAGCGGAA AGAGAAGAAA GCACAGAAGG AGAAGGACAA ACTGCCTGTC AGCACGACGA CGGTGGACGA CCACATGCCG CCCATTATGC AGTGTGAACC
                                                                 EcR (wt)
7501 TCCACCTCCT GAAGCAGCAA GGATTCACGA AGTGGTCCCA AGTTTCTCT CCGACAAGCT GTTGGTGACA AACCGGCAGA AAAACATCCC CCAGTTGACA
                                                                 EcR (wt)
7601 GCCAACCAGC AGTTCCTTAT CGCCAGGCTC ATCTGGTACC AGGACGGGTA CGAGCAGCCT TCTGATGAAG ATTTGAAGAG GATTACGCAG ACGTGGCAGC
                                                                 EcR (wt)
7701 AAGCGGACGA TGAAAACGAA GAGTCGGACA CTCCCCTTCG CCAGATCACA GAGATGACTA TCCTCACGGT CCAACTTATC GTGGAGTTCG CGAAGGGATT
                                                                 EcR (wt)
7801 GCCAGGGTTC GCCAAGATCT CGCAGCCTGA TCAAATTACG CTGCTTAAGG CTTGCTCAAG TGAGGTAATG ATGCTCCGAG TCGCGCGACG ATACGATGCG
                                                                 EcR (wt)
7901 GCCTCCGACA GTGTTCTGTT CGCGAACAAC CAAGCGTACA CTCGCGACAA GCTGCATGG CCTACGTCAT CGAGGATCTA CTGCACTTCT
                                                                 EcR (wt)
8001 GCCGGTGCAT GTACTCTATG GCGTTGGACA ACATCCATTA CGCGCTGCTC ACGGCTGTCG TCATCTTTTC TGACCGGCCA GGGTTGGAGC AGCCGCAACT
                                                                 EcR (wt)
8101 GGTGGAAGAG ATCCAGCGGT ACTACCTGAA TACGCTCCGC ATCTATATCC TGAACCAGCT GAGCGGGTCG GCGCGTTCGT CCGTCATATA CGGCAAGATC
                                                                 EcR (wt)
8201 CTCTCAATCC TCTCTGAGCT ACGCACGCTC GGCATGCAAA ACTCCAACAT GTGCATCTCC CTCAAGCTCA AGAACAGAAA GCTGCCGCCT TTCCTCGAGG
                                                                 EcR (wt)
8301 AGATCTGGGA TGTGGCGGAC ATGTCGCACA CCCAACCGCC GCCTATCCTC GAGTCCCCCA CGAATCTCTA GCCCCTGCGC GCACGCATCG CCGATGCCGC
                                                                                                                    NosT
8401 GTCCGGCCGC GCTGCTCTGA GAATTCGATA TCAAGCTTCT TGCAGAGATC TGCAGAGATC TACGCGTTAA GCTTAATTCC CGATCGTTCA AACATTTGGC
                                                                 NosT
8501 AATAAAGTTT CTTAAGATTG AATCCTGTTG CCGGTCTTGC GATGATTATC ATATAATTTC TGTTGAATTA CGTTAAGCAT GTAATAATTA ACATGTAATG
                                                                 NosT
```

Fig. 3D

```
8601 CATGACGTTA TTTATGAGAT GGGTTTTTAT GATTAGAGTC CCGCAATTAT ACATTTAATA CGCGATAGAA AACAAAATAT AGCGCGCAAA CTAGGATAAA
          NosT                                                                              5xGAL4 Response Element 8701 TTATCGCGCG CGGTGTCATC TATGTTACTA GATCGGGGAC TAGTAAGCCC GGCCGCTTGG ATCCGCTCGG AGGACAGTAC TCCGCTCGGA GGACAGTACT
                       5xGAL4 Response Element              SpeI     FseI                        Minimal 35S promoter 8801 CCGCTCGGAG GACAGTACTC CGCTCGGAGG CAGTACTCCG CTCGGAGGAC AGTACTCCGA TCCGTCAGAT CTGCAAGACC CTTCCTCTAT ATAAGGAAGT
          Minimal 35S promoter                                                                  ETP1

8901 TCATTTCATT TGGAGAGGAC ACGCTGAAAC ATGACGATAC CGGATCTCTG TAACGATTTG GTCGATGAGA TACTCTGTCG CGTTCCGGCG AGGAATCTGA
                                                         ETP1

9001 AACGGTTACG ATCTACCAGC AAACGATGGA ACCGTTTATT CAAAGATGAT AGGAGATTCG CAAGAGAGCA CATGCATAAA GCCCCAAAGG AGTATCTACC
                                                         ETP1

9101 TCTCATGTTG ACAAGCGGAG ATCAACTCTG TCCGGTGAGC ACAGGATCTG ATCAATCTCC AAGGAGATGT TCCTTCTGTA GTGTTAAAGA GAGAGCTTAG CCTACCAGAT
                                                         ETP1

9201 CCGGATTATT CACATCAATT CGATATAGGT CGAGTCTTTC ACTGCGACGG CTTATTGGTA TGCAACCACG TAGGCAAGAA TCCCCGATAC GGATCTAAAA
                                                         ETP1

9301 TCGTGGTTTG GAACCCGCTG ACTGGTCAAA CCAGGTGGAT CGAAGCCGGC TATCGTTGGA AGGAATACGA AGTCAGATTT GTTCTCGGAT ACTGCTACCA
                                                         ETP1

9401 GCAAGACGAG AACAATTCCT GCAGTAAAAA AATCTACAAA ATTTTGTGTT TTTATCCTAA TGGCCAAGAT ACAGAAATCT ACGAGCTTAA CTACTCTGAT
                                                         ETP1

9501 AGGTGGACAA GGACGATTCC TGATGGTGAT CTCACTCCAG GCTGGACCTT GATATACTCA GAGCAGACCG TGTCTATGAA TGGAAATCTT TACTTGTTTG
                                                         ETP1

9601 CTTCGGAGAA ATCAAAACCC CATCCTTGGCG TGTCCTTGCT CAGATTTGAT TTCTCAACAG AGAAATCATC TCTATGTGTG ACTCTTCCCT ATCAGCGTCC
```

Fig. 3E

```
                                    ETP1
9701  AAGGTATGATGAA ATTTTGAGTA TTTCCGCCGT TAGAGGAGGA GAGAATCTTT CTCTGTTGTT GCAGCTCGAT TTTGAATCTA AGACTGAGAT ATGGGTGACG
                                                                              ETP1
9801  AATAAGATTG ATGACACCAC CACCAAAGGA GCAGCAGTCT CTTGGACCAA GGTCCTAGCA TTTGATTTAA GCCCTGATCT TCAATTATTT TCGGAGGAGG
                                                                              ETP1
9901  TAAATTTTTT GCTTGACGAG GATAAGAAAG TCGCTGTGTG TTGTGAGAGA TGGTTGGAAC CGCAAGAGCA CCACAGGTAC CAGTGCAGGA GAGAGTACAA
                                                                              ETP1
10001 GATCACCGAC AAGATATACA TTCTCGGGGA GGATAATAAA GTCGATGAAG TAGGTTCTGG AGAGGGAGAG GCTACACAGATT CACTTGAAGG AATTTCGCAA
                                                                              ETP1
10101 GTTATTCTCA ATTACGCTCC AAGTTTGGTC CAAATCGAGC AAGCCGGAGG AGGCAAAAACA AAAAGAGGTG ACGACTAAGC GGCCGCTAGG GCATGTCTAG
                                                              35S Terminator
10201 AAGTCCGCAA AAATCACCAG TCTCTCTCTA CAAATCTCTATT TTTCTCCAGA ATAATGTGTG AGTAGTTCCC AGATAAGGGA ATTAGGGTTC
                                                              35S Terminator
10301 TTATAGGGTT TCGCTCATGT GTTGAGCATA TAAGAAACCC TTAGTATGTA TTTGTATTTG TAAAATACTT CTATCAATAA AATTTCTAAT TCCTAAAACC
      35S Terminator
10401 AAAATCCAGT GACTGCAGGC ATGCAAGCTT CATGAGTATA ACTATAATTA TAAAGCAATG ATTAGAATCT GACAAGGATT CTGGAAAATT ACATAAAGGA AAGTTCATAA
                                                                              rbcSEp polyA
10501 TTCATACTCA ACTACAAAATC CATGAGTATA ACTACTTGTA TTCAGTAACA TATCACTTGTA TTCAGTAACA CATACTTGTA TTCAGCTT TTCTAGGTCT GAAAATATAT TTGTTGCCTA GTGAATAAGC ATAATGGTAC
                                                                              rbcSEp polyA
10601 ATGTCTAAAA CACAAGAGGA CATACTTGTA TTCAGTAACA TTTGCAGCTT TTCTAGGTCT GAAAATATAT TTGTTGCCTA GTGAATAAGC ATAATGGTAC
                                                                              rbcSEp polyA
10701 AACTACAAGT GTTTTACTCC TCATATTAAC TTCGGTCATT AGAGGCCACG ATTTGACACA TTTTTACTCA AAACAAAATG TTTGCATATC TCTTATAATT
```

Fig. 3F

```
                   rbcSEp polyA
10801 TCAAATTCAA CACACAACAA ATAAGAGAAA AAACAAATAA TATTAATTTG AGAATGAACA AAAGGACCAT ATCATTCATT AACTCTTCTC CATCCATTTC
                   rbcSEp polyA
10901 CATTTCACAG TTCGATAGCG AAAACCGAAT AAAAAAACACA GTAAATTACA AGCACACAA ATGGTACAAG AAAAACAGTT TTCCCAATGC CATAATACTC
                   rbcSEp polyA
11001 AAACTCAGTA GGATTCTGGT GTGTGCGCAA TGAAACTGAT GCATTGAACT TGACGAACGT TGTCGAAACC GATGATACGA ACGAAAGCTC TAGAGGATCA
                                                                                                   DEF ORF
11101 ATTCGAGCTC TTAGGTCGAC CCACGTTTGC CAAAACCAAC TCCTGCTCTC CTTTTTTGTC CTATCAAGAA CTTGATCCGT CATTCTGTCA CTTGGCAATC CAGTTTTTC
                   DEF ORF
11201 TTCGTACTTC TTTTCTAGGG CCTCTAGCTC AGGTAAACGT GATAGACTGA TTGAAAAATCT TTCACCAGTA ATATCCCTTG CATCAATCTT GACAGATTGT GGTCGAACAA
                   DEF ORF
11301 TCGTGCTGAA AGATTCGTGC AAGGAGAGC ATCCTTCATC AAACGGTACT AATTTATCGG GACCTACTTG TGGTGCTGAG AGCCCAATGC CATCCGTTTT GTACATAACA
                   DEF ORF
11401 CTTCAGCATA GATCCCCGGG AAGGAGAGC ATCCTTCATC AAACGGTACT AATTTATCGG GACCTACTTG TGGTGCTGAG AGCCCAATGC CATCCGTTTT GTACATAACA
                   DEF ORF
11501 TCCTTCTCCA GGCTCTCCAG CTGGATTAAA CACCATGAGT TGAACATTGA GACCTACTTG TGGTGCTGAG AGCCCAATGC CATCCGTTTT GTACATAACA
                   DEF ORF
11601 TCAAACATAG CATCAACCAA GTTCTTTAAA TTCTCGTCAA AATATCAAT CCTCTTGTTC TTAGCCCGTA GTATAGGATC CGGATACTCA ACAATCTTCA
                   DEF ORF
11701 AAGGCGTCTC AAATTGAACA TCAGTAGCTG AAGCTACTTT ATCGTCTTTA CGGAGACGC GCTTTACTTC TGCGCGGACC GAACATGTCA GAGGACTGGT
                                                                                                   AgeI
11801 CCGGTTCACA GTAGAGCAGA ACGTGACCGT GGATTTGAGC CGACCATAAC CGGCAGAGAG AGTAGTAGCT CGGCGAGATA AAACCGGTAG GAGTATGCGA
```

Fig. 3G

```
                                                                                             DEF ORF
11901  GAGAGTGGTG GAGCTTGGAG GAAGCAGTTA CAGACGGCTC CCATGGTGGA AGTATTTGAA AAATAAAAAG ATCCGCTCGA GGATCCAAGC
              DEF ORF
12001  TTAGATGAGA GATTTCGATT CCGATTTTGA TTTCGATTCC GATTTTGATT TCGATTGATC TCTTCCTTCT GATTTGTGTT GGAAATTCTT
                                                         MMV promoter -197 to +63
12101  GTGGGATTAG ACGTCATGGC TTACGTCATT TCCTTCGTCC TGTTGCTCAC TGATTGAGCT GTGAGTGGAG GGACCACTGG AAGATGCTTC ACTAATTTTC
                                                         MMV promoter -197 to +63
12201  TTAGTGGAGG GACCGGCTTC ACATGCTTCA CACAAGTGGC TGTCGGGCAT CATCTTTTTT AGCTTTTGAC AAAGCAATGT TTTAGTGGTG GCTCCCACTC
                                                         MMV promoter -197 to +63
12301  TTATCTTCAA CATTATTATC TTATCTTCAA AGGACGATAA GATGTTGATG TCTGTGGACG AAGTTGGGAT TAGACGTCAT GGCTTACGTC ATTTCCTTCG
                            MMV promoter -197 to +63                                                  enhancer
12401  TCCTGTTGCT CACTGATTGA GCTGTGAGTG GAGGACCAC TGGAAGATGC TTCACTAATT TTCTTAGTGG AGGGACCGGC TTCTCATGCT TCACACAAGT
                                                                              enhancer
12501  GGCTGTGCGG CATCATCTTT TTTAGCTTTT GACAAAGCAA TGTTTTAGTG GGGGCTCCCA CTCTTATCTT CAACATTATT ATCTTATCTT CAAAGGACGA
                                                                   enhancer
12601  TAAGATGTTG ATGTCTGTGG ACGAAGTTGA CGAATTCGA CCTGCAGGCA TGCAAGCTTG GCGTAATCAT GGTCATAGCT GTTTCCTGTG TGAAATTGTT
              enhancer
12701  ATCCGCTCAC AATTCCACAC AACATACGAG CCGGAAGCAT AAAGTGTAAA GCCTGGGGTG CCTAATGAGT GAGCTAACTC ACATTAATTG CGTTGCGCTC
12801  ACTGCCCGCT TTCCAGTCGG GAAACCTGTC GTGCCAGCTG CATTAATGAA TCGGCCAACG CGCGGGGAGA GGCGGTTTGC GTATTGGGCG AAAGACAAAA
12901  GGGCGACATT CAACCGATTG AGGGAGGGAA GGTAAATATT GACGGAAATT ATTCATTAAA GGTGAATTAT CACCGTCACC GACTTGAGCC ATTTGGGAAT
13001  TAGAGCCAGC AAAATCACCA GTAGCACCAT TACCATTAGC AAGGCCGGAA ACGTCACCAA TGAAACCATC GATAGCAGCA CCGTAATCAG TAGCGACAGA
13101  ATCAAGTTTG CCTTTAGCGT CAGACTGTAG CGCGTTTTCA TCGGCATTTT CGGTCATAGC CCCCTTATTA GCGTTTGCCA TCTTTTCATA ATCAAAATCA
13201  CCGGAACCAG AGCCACCACC GGAACCGCCT CCCTCAGAGC CGCCACCCTC AGAACCGCCA CCCTCAGAGC CACCACCCTC AGAGCCGCCA CCAGAACCAC
13301  CACCAGAGCC GCCGCCAGCA TTGACAGGAG GCCGATCTA GTAACATAGA TGACACCGCG CGCGATAATT TATCCTAGTT TGCGCGCTAT ATTTTGTTTT
```

Fig. 3H

```
                                                               Nos terminator
13401  CTATCGCGTA TTAAATGTAT AATTGCGGGA CTCTAATCAT AAAAACCCAT CTCATAAATA ACGTCATGCA TTACATGTTA ATTATTACAT GCTTAACGTA
                                                                                  Nos terminator
13501  ATTCAACAGA AATTATATGA TAATCATCGC AAGACCGGCA ACAGGATTCA ATCTTAAGAA ACTTTATTGC CAAATGTTTG AACGATCGGG GATCATCCGG
                                                     Nos terminator
13601  GTCTGTGGCG GGAACTCCAC GAAAATATCC GAACGCAGCA AGATATCGCG GTGCATCTCG GTCTTGCCTG GGCAGTCGCC GCCGACGCCG TTGATGTGGA
            ApaI
13701  CGCCGGGCCC GATCATATTG TCGCTCAGGA TCGTGGCGTT GTGCTTGCTG GCCGTTGCTG TCGTAATGAT ATCGGCACCT TCGACCGCCT GTTCCGCAGA
13801  GATCCCGTGG GCGAAGAACT CCAGCATGAG ATCCCCCGCG TGGAGGATCA TCCAGCCGGC GTCCCGGAAA ACGATTCCGA AGCCCAACCT TTCATAGAAG
13901  GCGGCGGTGG AATCGAAATC TCGTGATGGC AGGTTGGGCG TCGCTTGGTC GGTCATTTCG AACCCCAGAG TCCCGCTCAG AAGAACTCGT CAAGAAGGCG
                                                                                                       NPT II
14001  ATAGAAGGCG ATGCGCTGCG AATCGGGAGC GGCGATACCG TAAAGCACGA GGAAGCGGTC AGCCCATTCG CCGCCAAGCT CTTCAGCAAT ATCACGGGTA
                                                                                    NPT II
14101  GCCAACGCTA TGTCCTGATA GCGGTCCGCC ACACCCAGCC GGCCACAGTC GATGAATCCA GAAAAGCGGC CATTTTCCAC CATGATATTC GGCAAGCAGG
                                                                NPT II
14201  CATCGCCATG GGTCACGACG AGATCATCGC CGTCGGGCAT GCGCGCCTTG AGCCTGGCGA ACAGTTCGGC TGGCGCGAGC CCCTGATGCT CTTCGTCCAG
                                                NPT II
14301  ATCATCCTGA TCGACAAGAC CGGCTTCCAT CCGAGTACGT GCTCGCTCGA TGCGATGTTT CGCTTGGTGG TCGAATGGGC AGGTAGCCGG ATCAAGCGTA
                                    NPT II
14401  TGCAGCCGCC GCATTGCATC AGCCATGATG GATACTTTCT CGGCAGGAGC AAGGTGAGAT GACAGGAGAT CCTGCCCCGG CACTTCGCCC AATAGCAGCC
                    NPT II
14501  AGTCCCTTCC CGCTTCAGTG ACAACGTCGA GCACAGCTGC GCAAGGAACG CCCGTCGTGG CCAGCCACGA TAGCCGCGCT GCCTCGTCCT GCAGTTCATT
                    NPT II
14601  CAGGGCACCG GACAGGTCGG TCTTGACAAA AGAACCGGGC GCCCCCTGCG CTGACAGCCG GAACACGGCG GCATCAGAGC AGCCGATTGT CTGTTGTGCC
```

Fig. 3I

```
14701 CAGTCATAGC CGAATAGCCT CTCCACCCAA GCGGCCGGAG AACCTGCGTG CAATCCATCT TGTTCAATCA TGCGAAACGA TCCAGATCCG GTGCAGATTA
                                            NPT II                                                          Nos promoter
                                                                                                            NheI 14801 TTTGGATTGA GAGTGAATAT GAGACTCTAA TTGGATACCG AGGGGAATTT ATGGAACGTC AGTGGAGCAT TTTTGACAAG AAATATTTGC TAGCTGATAG
                                                              Nos promoter 14901 TGACCTTAGG CGACTTTTGA ACGCGCAATA ATGGTTTCTG ACGTATGTGC TTAGCTCATT AAACTCCAGA AACCCGCGGC TGAGTGGCTC CTTCAACGTT
                                                              Nos promoter 15001 GCGGTTCTGT CAGTTCCAAA CGTAAAACGG CTTGTCCCGC GTCATCGGCG GGGGTCATAA CGTGACTCCC TTAATTCTCC GCTCATGATC
                                                              Nos promoter
```

Fig. 4B

```
                                                                    ATAGTT TAAACTGAAG GCGGGAAACG
                      G10-90 promoter
6301
      ACAATCTGAT CCAAGCTCAA GCTAAGCTTG CATGCCTGCA GGATATCGTG TGCCCAAGCT CGCCACGTGC CGCCACGTGC
                      G10-90 promoter                              G10-90 promoter
6401  CTCTAGAGGA TCCATCTCCA CTGACGTAAG CTGATGACGCA CAATCCCACT ATCCTTCGCA AGACCCTTCC TCTATATAAG GAAGTTCATT TCATTTGGAG
                                                                                          Gal4
6501  AGGACACGCT GGGATCCCCA CCATGGATCC GCCACCATGC TAGCCCACCA TGAAGCTACT GTCTTCTATC GAACAAGCAT GCGATATTTG CCGACTTAAA
6601  AAGCTCAAGT GCTCCAAAGA AAAACCGAAG TGCGCCAAGT GTCTGAAGAA CAACTGGGAG TGTCGCTACT CTCCCAAAAC CAAAAGGTCT CCGCTGACTA
                                                         Gal4
6701  GGGCACATCT GACAGAAGTG GAATCAAGGC TAGAAAGACT TTTCTACTGA TTTTTCCCTCG AGAAGACCTT GACATGATTT TGAAAATGGA
                                                         Gal4
6801  TTCTTTACAG GATATAAAAG CATTGTTAAC AGGATTATTT GTACAAGATA ATGTGAATAA AGATGCCGTC ACAGATAGAT TGGCTTCAGT GGAGACTGAT
                                         HpaI                                       Gal4                          VP16
6901  ATGCCTCTAA CATTGAGACA GCATAGAGCA AGTGCGACAT CATCATCGGA AGAGAGTAGT AAAGACAGTT AACAAAAGGTC GACTGTATCC ATGGCCCCCC
                                                                     VP16
7001  CGACCGATGT CAGCCTGGGG GACGAACTCC ACTTAGACGG GCGAGGACGTG ATGCCGACGC GCTAGACGAT TTCGATCCGA ACATGTTGGG
                                                                      VP16
7101  GGACGGGGAT TCCCCAGGTC CGGGATTTAC CCCCCACGAC TCCGCCCCCT ACGGCCGCTCT ACGGGCGCTCT GGATATGGCC GACTTCGAGT TTGAGCAGATG TTTACCGAT
7201
```

Fig. 4C

| | VP16 | | | | | EcR (wt) | |
|---|---|---|---|---|---|---|---|
| 7301 | GCCCTTGGAA | TTGACGAGTA | CGGTGGGAAG | CTTCTAGGTA | CCTCTAGAAG | AATATCGTGG | CCTGAGTGCG | TAGTACCCGA | GACTCAGTGC | GCCATGAAGC |
| 7401 | GGAAAGAGAA | GAAAGCACAG | AAGGAGAAGG | ACAAACTGCC | TGTCAGCACG | ACGACGGTGG | ACGACCACAT | GCCGCCCATT | ATGCAGTGTG | AACCTCCACC |
| 7501 | TCCTGAAGCA | GCAAGGATTC | ACGAAGTGGT | CCCAAGGTTT | CTCTCCGACA | AGCTGTTGGA | GACAAACCGG | CAGAAAAACA | TCCCCCAGTT | GACAGCCAAC |
| 7601 | CAGCAGTTCC | TTATCGCCAG | GCTCATCTGG | TACCAGGACG | GGTACGAGCA | GCCTTCTGAT | GAAGATTTGA | AGAGGATTAC | GCAGACGTGG | CAGCAAGCGG |
| 7701 | ACGATGAAAA | CGAAGAGTCG | GACACTCCCT | TCCGCCAGAT | CACAGAGATG | ACTATCCTCA | CGGTCCAACT | TATCGTGGAG | TTCGCGAAGG | GATTGCCAGG |
| 7801 | GTTCGCCAAG | ATCTCGCAGC | CTGATCAAAT | TACGCTGCTT | AAGGCTTGCT | CAAGTGAGGT | AATGATGCTC | CGAGTCGCGC | GACGATACGA | TGCGGCCTCC |
| 7901 | GACAGTGTTC | TGTTCGCGAA | CAACCAAGCG | TACACTCGCG | ACAAACTACCG | CAAGGCTGGC | TCATCGAGGA | TCTACTGCAC | TTCTGCCGGT |
| 8001 | GCATGTACTC | TATGGCGTTG | GACAACATCC | ATTACGCGCT | GCTCACGGCT | GTCGTCATCT | TTTCTGACCG | GCCAGGGTTG | GAGCAGCCGC | AACTGGTGGA |
| 8101 | AGAGATCCAG | CGGTACTACC | TGAATACGCT | CCGCATCTAT | ATCCTGAACC | AGCTGAGCGG | GTCGGCGCGT | TCGTCCGTCA | TATACGGCAA | GATCCTCTCA |
| 8201 | ATCCTCTCTG | AGCTACGCAC | GCTCGGCACA | CAAAACTCCA | ACATGTGCAT | CTCCCTCAAG | CTCAAGAACA | GAAAGCTGCC | GCCTTTCCTC | GAGGAGATCT |
| 8301 | GGGATGTGGC | GGACATGTCG | CACACCCAAC | CGCCGCCCAT | CCTCGAGTCC | CCCACGAATC | TCTAGCCCCT | GGGGCACGC | ATCGCCGATG | CCGGTCCGG |
| | | | | | | | NosT | | | |
| 8401 | CCGCGCTGCT | CTGAGAATTC | GATATCAAGC | TTCTAGACCC | GGGCTGCAGA | GATCTACGCG | TTAAGCTTAA | TTCCCGATCG | TTCAAACATT | TGGCAATAAA |

Fig. 4D

```
8501  GTTCTTAAG ATTGAATCCT GTTGCCGGTC TTGCGATGAT TATCATATAA TTTCTGTTGA ATTACGTTAA GCATGTAATA ATTACATGT AATGCATGAC
                NosT                                              NosT

8601  GTTATTTATG AGATGGGTTT TTATGATTAG AGTCCCGCAA TTATACATTT AATACGCGAT AGAAAACAAA ATATAGCGCG CAAACTAGGA TAAATTATCG
          NosT                                                                          5xGAL4 Response Element
                           SpeI            FseI 8701  CGGCGCGGTGT CATCTATGTT ACTAGATCGG GGACTAGTAA GGCCGGCCGC TTGGATCCGC TCGGAGGACA GTACTCCGCT CGGAGGACAG TACTCCGCTC
                            5xGAL4 Response Element                                                    Minimal 35S promoter 8801  GGAGGACAGT ACTCCGCTCG AGGACAGTAC TCCGCTCGGA AGGACAGTAC TCCGATCCGTC AGATCTGCAA GACCCTTCCT CTATATAAGG AAGTTCATTT
         Minimal 35S promoter                                          ETP2

8901  CATTTGGAGA GGACACGCTG AACCATGAAG ACAATACAGG AGCAGCTTCC AAATGACTTG GTAGAGGAGA TACTCTGTCG CGTTCCGGCA ACATCTCTGA
                                                                      ETP2

9001  GACGTTTACG ATCGACTTGC AAAGCATGGA ACCGTTTATT CAAAGGTGAT CGGATATTAG CAAGTAAGCA TTTTGAAAAA TCCGCAAAAC AGTTTAGATC
                                                                      ETP2

9101  TCTATCGTTA AGGAATGATT ACAGGATTTT TCCGATTAGC TTCAATCTCC ATGGAAATAG TCCATCTCTA GAGCTTAAAA GTGAGCTAAT CGATCCTCAT
                                                                      ETP2

9201  TCTAAGAATT CAGCTGCTCC ATTCGAAATA TCTCGAGTCA TTCACTCTGA GGGATTGTTG TTGTGCTCCT CCCAATTGGA CGAATCTAGA GTCGTGGTTT
                                                                      ETP2

9301  GGAATCCTTT AACCGGTGAA ACCAGTGTGA TCAGAACCGG CGATTTTCGC CAAAAAGGCC GTAGCTTTGA TGTCGGGTAC TACTACCAAA AAGACAAGAG
                                                                      ETP2

9401  ATCCTGGATC AAGAGCTACA AACTCTGTG CTATTATCGT GGTACCAAAT ATTTTGAAAT CTACGATTTT GACTCTGATT CATGGAGGAT TCTTGATGAT
                                                                      ETP2

9501  ATTATCGCTC CACGGGGAG TATTGGATAC TCGGAACTTA GCGTGTCTCT GAAAGGAAAT ACTTACTGGT TCGCTAAAGG TGTAACAGAA GAGCGGCCCC
```

Fig. 4E

```
                 ETP2
9601  GCACCATATC ATTGCTCAAA TTTGATTTTT ATACAGAGAA ATCTGTACCT GTGCTTCTTC CCTATCAGAG TCGTCGTCTT TTCCAAGCTA GTAGCCTTTC
                                                 ETP2
9701  TGTTGTTAGA GAAGATAAAC TTTCTGTGTT ATTGCAGCTA GATCAAAGTT CCAAGACTGA GATATGGGTG ACAAATGTGA TTGATGAGAC CACCAAAGA
                                                                                                   AvrII
                                                                      ETP2
9801  GCAGTTTCTT GGACCAAGGT CTTAGCATTG GATTTGAGCC CTCATCTTCA GATTGGGAAT GATGGAAGTT TCTTCCTAGG CGAGGATAAG AAAGTCGTCA
                                                                 ETP2
9901  TGTTCTGTGA GAATTGATT GATGAGAACA AGTCAAAGA CATGGTCTAC ATTGTTGGGG AGGATAATGT TGTCACAGAA GTGGGATTTG GAGTAGATGA
10001 AATGGATGGA TGTCGGGCAG TTATTCTTAA TTATGTTCCA AGTTTGGTTC AAATCGAGCG AGCTGGAGGC AACAGGAAAA GAGGGCACTA AGCGGCGCT
                                                          35S Terminator
10101 AGGGCATGTC TAGAAGTCCG CAAAAATCAC CAGTCTCTCT CTACAAATCT ATCTCTCTCT ATTTTTCTCC AGAATAATGT GTGAGTAGTT CCCAGATAAG
                                                          35S Terminator
10201 GGAATTAGGG TTCTTTATAGG GTTTCGCTCA TGTGTTGAGC ATATAAGAAA CCCTTAGTAT GTATTTGTAT TTGTAAAATA CTTCTATCAA TAAAATTCT
                  35S Terminator
10301 AATTCCTAAA ACCAAAATCC AGTGACTGCA CCGTCGACGA CTTATCGATA TTATAAGCA ATGATTAGAA TCTGACAAGG ATTCTGGAAA ATTACATAAA
                                                                                              rbcSEp polyA
10401 ATTAAAAAAT ATTTTCATAC TCAACTACAA ATCCATGAGT ATAACTATAA TTATAAGCA ATGATTAGAA TCTGACAAGG ATTCTGGAAA ATTACATAAA
                                                                                rbcSEp polyA
10501 GGAAAGTTCA TAAATGTCTA AAACACAAGA GGACATACTT GTATTCAGTA ACATTTGCAG CTTTTCTAGG TCTGAAAATA TATTTGTTGC CTAGTGAATA
                                                                 rbcSEp polyA
10601 AGCATAATGG TACAACTACA AGTGTTTTAC TCCTCATATT AACTTCGGTC ATTAGAGGCC ACGATTTGAC ACATTTTTAC TCAAAACAAA ATGTTTGCAT
```

Fig. 4F

```
                      rbcSEp polyA
10701 ATCTCTTATA ATTTCAAATT CAACACACAA CAAATAAGAG AAAAAACAAA TAATATTAAT TTGAGAATGA ACAAAAGGAC CATATCATTC ATTAACTCTT
                      rbcSEp polyA
10801 CTCCATCCAT TTCCATTTCA CAGTTCCGATA GCGAAAACCG AATAAAAAAC ACAGTAAATT ACAAGCACAA CAAATGGTAC AAGAAAAACA GTTTTCCCAA
                      rbcSEp polyA
10901 TGCCATAATA CTCAAACTCA GTAGGATTCT GGTGTGTGCG CAATGAAACT GATGCATTGA ACTTGACGAA CGTTGTCGAA ACCGATGATA CGAACGAAAG
                      rbcSEp polyA
11001 CTCTAGAGGA TCAATTCGAG CTCTTAGGTC GACCCACGTT TGCCAAAACC AACTCCTGCT CTCCTTTTTT GTCGTGCTTC TACTCTTTCA GGGCTTGGCA
                                                                    DEF ORF
11101 ATCCAGTTTT TTCTTTTCTA TTCTTCGTAC GGGCCTCTAG CTGTGATAGAC CGTGATAGAC GAACTGGATC CGTCATTCTG TCAAAGAAGA GAACTCCCTC
      ......                                                         DEF ORF
11201 CAGATGGTCG TATTCGTGCT GAAAGATTCG TGCAGTAAAA CGTGATAGAC TGATTGAAAA TCTTTCACCA GTAATATCCC TTGCATCAAT CTTGACAGAT
                                                                    DEF ORF
11301 TGTGGTCGAA CAACTTCAGC ATAGATCCCC GGGAAGGAGA GGCATCCTTC CAGCTGGATT AAACACCATG AGTTGAACAT CGGAATATTT CTTGATTTTC GGATTACAA
                                                                    DEF ORF
11401 GGACAATTTC TTTTCCTTCT CCAGGCTCTC CAGCTGGATT AAACACCATG AGTTGAACAT CAAAAATATC AATCCTCTTG TTGTGGTGCT GAGAGCCCAA TGCCATCCGT
                                                                    DEF ORF
11501 TTTGTACATA ACATCAAACA TAGCATCAAC CAAGTTCTTT AAATTCTCGT CAAAAATATC TTTATCGTCT TTACGCGAGA CGCGCTTTAC TTCTGCGCGG ACCGAAGATG
                                                                    DEF ORF
11601 TCAACAATCT TCAAAGGCGT CTCAAATTGA ACATCAGTAG CTGAAGCTAC TTTATCGTCT TTACGCGAGA CGCGCTTTAC TTCTGCGCGG ACCGAAGATG
                                                                    DEF ORF
11701 TCAGAGGACT GGTCCGGTTC ACACAGAGAGC AGAACGTGAC CGTGGATTTG AGCCGACCAT AACCGGCAGA GAGAGTAGTA GCTCGGCGAG ATAAAACCGG
                                                                    DEF ORF
11801 TAGGAGTATG CGAGAGAGTG GTGGAGCTTG GAGGAAGCAG CTTACAGACGG CTCCCCATGGT GGAAGTATTT GAAAGAAAAT TAAAAATAAA AAGATCCGCT
```

Fig. 4G

```
                      DEF ORF
11901 CGAGGATCCA AGCTTAGATG AGAGATTTCG ATTCCGATTT TGATTTCGAT TCCGATTTTG ATTTCGATTG ATCTCTTCCT TCTGATTTGT GTTCCTTATA
                                                           MMV promoter -197 to +63
12001 TAAGGAAATT CTTGTGGGAT TAGACGTCAT GGCTTACGTC ATTTCCTTCG TCCTGTTGCT CACTGATTGA GCTGTGAGTG GAGGGACCAC TGGAAGATGC
                                                           MMV promoter -197 to +63
12101 TTCACTAATT TTCTTAGTGG AGGGACCGGC TTCACACAAGT TCACACATGCT GGCTGTCGGG CATCATCTTT TTTAGCTTTT GACAAAGCAA TGTTTTAGTG
                                                           MMV promoter -197 to +63
12201 GTGGCTCCCA CTCTTATCTT CAACATTATT ATCTTATCTT CAAAGGACGA TAAGATGTTG ATGTCTGTGG ACGAAGTTGG GATTAGACGT CATGGCTTAC
                                                                                                          enhancer
12301 GTCATTTCCT TCGTCCTGTT GCTCACTGAT TGAGCTGTGA GTGGAGGGAC CACTGGAAGA TGCTTCACTA ATTTTCTTAG TGGAGGGACC GGCTTCTCAT
                               enhancer
12401 GCTTCACACA AGTGGCTGTC GGGCATCATC TTTTTTTAGCT TTTGACAAAG CAATGTTTTA GTGGGGGCTC CCACTCTTAT CTTCAACATT ATTATCTTAT
                               enhancer
12501 CTTCAAAGGA CGATAAGATG TTCATGTCTG TGGACGAAGT TGACCGAATTT CGACCTGCAG GCATGCAAGC TTGGCGTAAT CATGGTCATA GCTGTTTCCT
12601 GTGTGAAATT GTTATCCGCT CACAATTCCA CACAACATAC GAGCCGGAAG CATAAAGTGT AAAGCCTGGG GTGCCTAATG AGTGAGCTAA CTCACATTAA
12701 TTGCGTTGCG CTCACTGCCC GCTTTCCAGT CGGGAAACCT GTCGTGCCAG CTGCATTAAT GAATCGGCCA ACGCGCGGGG AGAGCGGTT TGCGTATTGG
12801 GCCAAAGACA AAAGGGCGAC ATTCAACCGA TTGAGGGAGG GAAGGTAAAT CATTACCATT ATTGACGGAA ATTATTCATT AAAGGTGAAT TATCACCGTC ACCGACTTGA
12901 GCCATTTGGG AATTAGAGCC AGCAAAAATCA CCAGTAGCAC CCATGCCGTT TAGCGGAACG CGCATGAAACC CAATGAAACC ATCGATAGCA GCACCGTAAT
13001 CAGTAGCGAC AGAATCAAGT TTGCCTTTAG CGTCAGACTG TCATCGGCAT TTCGGTCAT AGCCCCCTTA TTAGCGTTTG CCATCTTTTC CTCAGAACCG
13101 ATAATCAAAA TCACCGGAAC CAGAGGAACC ACCGGCCACC CCTCCCCAG AGCCGGAACCG CCACCCTCAG AGCCACCACC ATTTATCCTA GTTTGCGCGC
13201 CCACCAGAAC CACCACCAGA GCCGCCGCCA GCATTGACAG GAGGCCCGAT CTAGTAACAT AGATGACACC GGCGCGATA ATTTATCCTA GTTTGCGCGC
                                                                       Nos terminator
13301 TATATTTTGT TTTCTATGCG GTATTAAATG TATAATTGCG GGACTCTAAT CATCTCATAA ATAACGTCAT CATAAAAACC GCATTACATG TTAATTATTA
                                                                       Nos terminator
13401 CATGCTTAAC GTAATTCAAC AGAAATTATA TGATAATCAT CGCAAGACCG GCAACAGGAT TCAATCTTAA GAAACTTTAT TGCCAAATGT TTGAACGATC
```

Fig. 4H

```
                       Nos terminator
13501 GGGGATCATC CGGGTCTGTG GCGGGAACTC CACGAAAAATA TCCGAACGCA GCAAGATATC GCGGTGCATC TCGGTCTTGC CTGGGCAGTC GCCGCCGACG
                                  ApaI
13601 CCGTTGATGT GGACGCCCGG CCCGATCATA TTGTCGCTCA GGATCGTGGC GTTGTGCTTG TCGGCCGTTG CTGTCGTAAT GATATCGGCA CCTTCGACCG
13701 CCTGTTCCGC AGAGATCCCG TGGGCGAAGA ACTCCAGCAT GAGATCCCCG CGCTGGAGGA TCATCCAGCC GGCGTCCCGG GGCGTCCCGG AAAACGATTC CGAAGCCAA
13801 CCTTTCATAG AAGGCGGGCG TGGAATCGAA ATCTCGTGAT GGCAGGTTGG GCGTCGCTTG GTCGGTCATT TCGAACCCCA GAGTCCCGCT CAGAAGAACT
                                                                                                 ≀≀     NPT II
13901 CGTCAAGAAG GCCGATAGAAG GCCGATGCGCT GCGAATCGGG AGCGGCGATA CCGTAAAGCA CGAGGAAGCG GTCAGCCCAT TCGCCGCCAA GCTCTTCAGC
14001 AATATCACGG GTAGCCAACG CTATGTCCTG ATAGCGGTCC GCCACACCA GCCGGCCACA GTCGATGAAT CCAGAAAAGC GGCCATTTTC CACCATGATA
                                                          NPT II
14101 TTCGGCAAGC AGGCATCGCC ATGGGTCACG ACGAGATCAT CGCCGTCGGG CATGCCGCC TTGAGCCTGG CGAACAGTTC GGCTGGCGCG AGCCCCTGAT
                                                          NPT II
14201 GCTCTTCGTC CAGATCATCC TGATCGACAA GACCGGCTTC CATCCGAGTA CGTGCTCGCT CGATGCGATG TTTCGCTTGG TGGTCGAATG GGCAGGTAGC
                                                          NPT II
14301 CGGATCAAGC GTATGCAGCC GCCGCATTGC ATCAGCCATG ATGGATACTT TCTCGGCAGG AGCAAGGTGA GATGACAGGA GATCCTGCCC CGGCACTTCG
                                                          NPT II
14401 CCCAATAGCA GCCAGTCCCT TCCCGCTTCA GTGACAACGT CGAGCACAGC TGCGCAAGGA ACGCCCGTCG TGGCCAGCCA CGATAGCCGC GCTGCCTCGT
                                                          NPT II
14501 CCTGCAGTTC ATTCAGGGCA CCGGACAGGT CGGTCTTGAC AAAAAGAACC GGGCGCCCCT GGCGTGACAG CCGGAACACG GCGGCATCAG AGCAGCCGAT
                                                          NPT II
14601 TGTCTGTTGT GCCCAGTCAT AGCCGAATAG CCTCTCCACC CAAGCGGCCG GAGAACCTGC GTGCAATCCA TCTTGTTCAA TCATGCGAAA CGATCCAGAT
                                                          NPT II                                                   Nos
14701 CCGGTGCAGA TTATTTGGAT TGAGAGTGAA TATGAGACTC TAATTGGATA CCGAGGGGAA TTTATGGAAC GTCAGTGGAG CATTTTTGAC AAGAAATATT
      promoter
```

Fig. 4I

```
                                   Nos promoter
14801 TGCTAGCTGA TAGTGACCTT AGGCGACTTT TGAACGCGCA ATAATGGTTT CTGACGTATG TGCTTAGCTC ATTAAACTCC AGAAACCCGC GGCTGAGTGG
                                        Nos promoter
14901 CTCCTTCAAC GTTGCGGTTC TGTCAGTTCC AAACGTAAAA CGGCTTGTCC CGCGTCATCG GCGGGGGTCA TAACGTGACT CCCTTAATTC TCCGCTCATG
                Nos promoter
15001 ATC
```

US 9,212,373 B2

SEQUENCE LISTING

<160> NUMBER OF SEQ ID NOS: 11

<210> SEQ ID NO 1
<211> LENGTH: 4038
<212> TYPE: DNA
<213> ORGANISM: Artificial
<220> FEATURE:
<223> OTHER INFORMATION: synthesized, based on Arabidopsis and
      Choristoneura fumiferana

<400> SEQUENCE: 1

```
atagtttaaa ctgaaggcgg gaaacgacaa tctgatccaa gctcaagcta agcttgcatg      60
cctgcaggat atcgtggatc caagcttgcc acgtgccgcc acgtgccgcc acgtgccgcc     120
acgtgcctct agaggatcca tctccactga cgtaagggat gacgcacaat cccactatcc     180
ttcgcaagac ccttcctcta tataaggaag ttcatttcat ttggagagga cacgctggga     240
tccccaccat ggcccccccg accgatgtca gcctggggga cgaactccac ttagacggcg     300
aggacgtggc gatggcgcat gccgacgcgc tagacgattt cgatctggac atgttggggg     360
acggggattc cccaggtccg ggatttaccc cccacgactc cgcccctac ggcgctctgg     420 atatggccga cttcgagttt gagcagatgt ttaccgatgc ccttggaatt gacgagtacg     480
gtgggaagct tctaggtacc tccagaagaa tatcaggcgg ggaattcggc gggatgaagc     540
tactgtcttc tatcgaacaa gcatgcgata tttgccgact taaaaagctc aagtgctcca     600
aagaaaaacc gaagtgcgcc aagtgtctga agaacaactg ggagtgtcgc tactctccca     660
aaaccaaaag gtctccgctg actagggcac atctgacaga agtggaatca aggctagaaa     720
gactggaaca gctatttcta ctgattttc ctcgagaaga ccttgacatg attttgaaaa     780
tggattcttt acaggatata aaagcattgt taacaggatt atttgtacaa gataatgtga     840
ataaagatgc cgtcacagat agattggctt cagtggagac tgatatgcct ctaacattga     900
gacagcatag aataagtgcg acatcatcat cggaagagag tagtaacaaa ggtcaaagac     960
agttgactgt atcgggaggc ggtgggatcc ggcctgagtg cgtagtaccc gagactcagt    1020
gcgccatgaa gcggaaagag aagaaagcac agaaggagaa ggacaaactg cctgtcagca    1080
cgacgacggt ggacgaccac atgccgccca ttatgcagtg tgaacctcca cctcctgaag    1140
cagcaaggat tcacgaagtg gtcccaaggt ttctctccga caagctgttg gtgacaaacc    1200
ggcagaaaaa catccccag ttgacagcca accagcagtt ccttatcgcc aggctcatct    1260
ggtaccagga cgggtacgag cagccttctg atgaagattt gaagaggatt acgcagacgt    1320
ggcagcaagc ggacgatgaa aacgaagagt cggacactcc cttccgccag atcacagaga    1380
tgactatcct cacggtccaa cttatcgtgg agttcgcgaa gggattgcca gggttcgcca    1440
```

```
agatctcgca gcctgatcaa attacgctgc ttaaggcttg ctcaagtgag gtaatgatgc    1500
tccgagtcgc gcgacgatac gatgcggcct ccgacagtgt tctgttcgcg aacaaccaag    1560
cgtacactcg cgacaactac cgcaaggctg gcatggccta cgtcatcgag gatctactgc    1620
acttctgccg gtgcatgtac tctatggcgt tggacaacat ccattacgcg ctgctcacgg    1680
ctgtcgtcat cttttctgac cggccagggt tggagcagcc gcaactggtg gaagagatcc    1740
agcggtacta cctgaatacg ctccgcatct atatcctgaa ccagctgagc gggtcggcgc    1800
gttcgtccgt catatacggc aagatcctct caatcctctc tgagctacgc acgctcggca    1860
tgcaaaactc caacatgtgc atctccctca agctcaagaa cagaaagctg ccgccttttcc    1920 tcgaggagat ctgggatgtg gcggacatgt cgcacaccca accgccgcct atcctcgagt    1980
cccccacgaa tctctagccc ctgcgcgcac gcatcgccga tgccgcgtcc ggccgcgctg    2040
ctctgagaat tcgatatcaa gcttctagac ccgggctgca gagatctacg cgttaagctt    2100
aattcccgat cgttcaaaca tttggcaata agtttcttta agattgaatc ctgttgccgg    2160
tcttgcgatg attatcatat aatttctgtt gaattacgtt aagcatgtaa taattaacat    2220
gtaatgcatg acgttattta tgagatgggt ttttatgatt agagtcccgc aattatacat    2280
ttaatacgcg atagaaaaca aaatatagcg cgcaaactag gataaattat cgcgcgcggt    2340
gtcatctatg ttactagatc ggggactagt aaggccggcc gcttggatcc gctcggagga    2400
cagtactccg ctcggaggac agtactccgc tcggaggaca gtactccgct cgaggacagt    2460
actccgctcg gaggacagta ctccgatccg tcagatctgc aagacccttc ctctatataa    2520
ggaagttcat ttcatttgga gaggacacgc tgaaccatga cgataccgga tctctgtaac    2580
gatttggtcg atgagatact ctgtcgcgtt ccggcgagga atctgaaacg gttacgatct    2640
accagcaaac gatggaaccg tttattcaaa gatgatagga gattcgcaag agagcacatg    2700
cataaagccc caaaggagta tctacctctc atgttgacaa gcgagtacag gatctgtccg    2760
gtgagcatca atctccaagg agatgttcct tctgtagtgt taaagagaga gcttagccta    2820
ccagatccgg attattcaca tcaattcgat ataggtcgag tctttcactg cgacggctta    2880
ttggtatgca accacgtagg caagaatccc cgatacggat ctaaaatcgt ggtttggaac    2940
ccgctgactg gtcaaaccag gtggatcgaa gccggctatc gttggaagga atacgaagtc    3000
agatttgttc tcggatactg ctaccagcaa gacgagaaca attcctgcag taaaaaaatc    3060
tacaaaattt tgtgttttta tcctaatggc caagatacag aaatctacga gcttaactac    3120
tctgataggt ggacaaggac gattcctgat ggtgatctca ctccaggctg gaccttgata    3180
tactcagagc agaccgtgtc tatgaatgga aatctttact tgtttgcttc ggagaaatca    3240 aaacccatc ttggcgtgtc cttgctcaga tttgatttct caacagagaa atcatctcta    3300
tgtgtgactc ttccctatca gcgtccaagg tatgaaattt tgagtatttc cgccgttaga    3360
ggaggagaga tctttctct gttgttgcag ctcgattttg aatctaagac tgagatatgg    3420
gtgacgaata agattgatga caccaccacc aaaggagcag cagtctcttg gaccaaggtc    3480
ctagcatttg atttaagccc tgatcttcaa ttattttcgg aggaggtaaa ttttttgctt    3540
gacgaggata agaaagtcgc tgtgtgttgt gagagatggt tggaaccgca agagcaccac    3600
aggtaccagt gcaggagaga gtacaagatc accgacaaga tatacattct cggggaggat    3660
aataaagtcg atgaagtagg ttctggagag ggagaggcta cagattcact tgaaggaatt    3720
tcgcaagtta ttctcaatta cgctccaagt ttggtccaaa tcgagcaagc cggaggaggc    3780
aaaacaaaaa gaggtgacga ctaagcggcc gctagggcat gtctagaagt ccgcaaaaat    3840
```

```
caccagtctc tctctacaaa tctatctctc tctatttttc tccagaataa tgtgtgagta    3900
gttcccagat aagggaatta gggttcttat agggtttcgc tcatgtgttg agcatataag    3960
aaacccttag tatgtatttg tatttgtaaa atacttctat caataaaatt tctaattcct    4020
aaaaccaaaa tccagtga                                                  4038
```

<210> SEQ ID NO 2
<211> LENGTH: 3951
<212> TYPE: DNA
<213> ORGANISM: Artificial
<220> FEATURE:
<223> OTHER INFORMATION: synthesized, based on Arabidopsis and
      Choristoneura fumiferana

<400> SEQUENCE: 2

```
atagtttaaa ctgaaggcgg gaaacgacaa tctgatccaa gctcaagcta agcttgcatg      60
cctgcaggat atcgtggatc caagcttgcc acgtgccgcc acgtgccgcc acgtgccgcc     120
acgtgcctct agaggatcca tctccactga cgtaagggat gacgcacaat cccactatcc     180
ttcgcaagac ccttcctcta tataaggaag ttcatttcat ttggagagga cacgctggga     240
tccccaccat ggatccgcca ccatgctagc ccaccatgaa gctactgtct tctatcgaac     300
aagcatgcga tatttgccga cttaaaaagc tcaagtgctc caagaaaaaa ccgaagtgcg     360
ccaagtgtct gaagaacaac tgggagtgtc gctactctcc caaaaccaaa aggtctccgc     420
tgactagggc acatctgaca gaagtggaat caaggctaga aagactggaa cagctatttc     480
tactgatttt tcctcgagaa gaccttgaca tgattttgaa aatggattct ttacaggata     540
taaaagcatt gttaacagga ttatttgtac aagataatgt gaataaagat gccgtcacag     600
atagattggc ttcagtggag actgatatgc ctctaacatt gagacagcat agaataagtg     660
cgacatcatc atcggaagag agtagtaaca aaggtcaaag acagttgact gtatccatgg     720 ccccccccgac cgtgtcagc ctgggggacg aactccactt agacggcgag gacgtggcga     780
tggcgcatgc cgacgcgcta gacgatttcg atctggacat gttggggac ggggattccc      840 caggtccggg atttaccccc cacgactccg cccctacgg cgctctggat atggccgact      900
tcgagtttga gcagatgttt accgatgccc ttggaattga cgagtacggt gggaagcttc     960
taggtacctc tagaagaata tcgtggcctg agtgcgtagt acccgagact cagtgcgcca    1020
tgaagcggaa agagaagaaa gcacagaagg agaaggacaa actgcctgtc agcacgacga    1080
cggtggacga ccacatgccg cccattatgc agtgtgaacc tccacctcct gaagcagcaa    1140
ggattcacga agtggtccca aggtttctct ccgacaagct gttggagaca aaccggcaga    1200
aaaacatccc ccagttgaca gccaaccagc agttccttat cgccaggctc atctggtacc    1260
aggacgggta cgagcagcct tctgatgaag atttgaagag gattacgcag acgtggcagc    1320
aagcggacga tgaaaacgaa gagtcggaca ctcccttccg ccagatcaca gagatgacta    1380
tcctcacggt ccaacttatc gtggagttcg cgaagggatt gccagggttc gccaagatct    1440
cgcagcctga tcaaattacg ctgcttaagg cttgctcaag tgaggtaatg atgctccgag    1500
tcgcgcgacg atacgatgcg gcctccgaca gtgttctgtt cgcgaacaac caagcgtaca    1560
ctcgcgacaa ctaccgcaag gctggcatgg cctacgtcat cgaggatcta ctgcacttct    1620
gccggtgcat gtactctatg gcgttggaca acatccatta cgcgctgctc acggctgtcg    1680
tcatcttttc tgaccggcca gggttggagc agccgcaact ggtggaagag atccagcggt    1740
actacctgaa tacgctccgc atctatatcc tgaaccagct gagcgggtcg cgcgttcgt     1800
```

```
ccgtcatata cggcaagatc ctctcaatcc tctctgagct acgcacgctc ggcatgcaaa    1860
actccaacat gtgcatctcc ctcaagctca agaacagaaa gctgccgcct ttcctcgagg    1920
agatctggga tgtggcggac atgtcgcaca cccaaccgcc gcctatcctc gagtccccca    1980
cgaatctcta gcccctgcgc gcacgcatcg ccgatgccgc gtccggccgc gctgctctga    2040
gaattcgata tcaagcttct agacccgggc tgcagagatc tacgcgttaa gcttaattcc    2100
cgatcgttca acatttggc aataaagttt cttaagattg aatcctgttg ccggtcttgc     2160
gatgattatc atataattc tgttgaatta cgttaagcat gtaataatta acatgtaatg    2220
catgacgtta tttatgagat gggtttttat gattagagtc ccgcaattat acatttaata    2280
cgcgatagaa acaaaatat agcgcgcaaa ctaggataaa ttatcgcgcg cggtgtcatc    2340
tatgttacta gatcggggac tagtaaggcc ggccgcttgg atccgctcgg aggacagtac    2400
tccgctcgga ggacagtact ccgctcggag gacagtactc cgctcgagga cagtactccg    2460
ctcggaggac agtactccga tccgtcagat ctgcaagacc cttcctctat ataaggaagt    2520
tcatttcatt tggagaggac acgctgaacc atgaagacaa tacaggagca gcttccaaat    2580
gacttggtag aggagatact ctgtcgcgtt ccggcaacat ctctgagacg tttacgatcg    2640
acttgcaaag catggaaccg tttattcaaa ggtgatcgga tattagcaag taagcatttt    2700
gaaaaatccg caaacagtt tagatctcta tcgttaagga atgattacag gattttccg      2760 attagcttca atctccatgg aaatagtcca tctctagagc ttaaaagtga gctaatcgat    2820
cctcattcta agaattcagc tgctccattc gaaatatctc gagtcattca ctgtgaggga    2880 tgttgttgt gctcctccca attggacgaa tctagagtcg tggtttggaa tcctttaacc     2940
ggtgaaacca ggtggatcag aaccggcgat tttcgccaaa aaggccgtag ctttgatgtc    3000
gggtactact accaaaaaga caagagatcc tggatcaaga gctacaaact cttgtgctat    3060
tatcgtggta ccaaatattt tgaaatctac gattttgact ctgattcatg gaggattctt    3120
gatgatatta tcgctccacg ggggagtatt ggatactcgg aacttagcgt gtctctgaaa    3180
ggaaatactt actggttcgc taaaggtgta acagaagagc ggccccgcac catatcattg    3240
ctcaaatttg attttatac agagaaatct gtacctgtgc ttcttcccta tcagagtcgt    3300 cgtctttttcc aagctagtag cctttctgtt gttagagaag ataaactttc tgtgttattg    3360
cagctagatc aaagttccaa gactgagata tgggtgacaa atgtgattga tgagaccacc    3420
aaaggagcag tttcttggac caaggtctta gcattggatt tgagccctca tcttcagatt    3480
gggaatgatg aagtttctt cctaggcgag ataagaaag tcgtcatgtt ctgtgagaaa     3540
ttgattgatg agaacaaggt caaagacatg gtctacattg ttggggagga taatgttgtc    3600
acagaagtgg gatttggagt agatgaaatg gatggatgtc gggcagttat tcttaattat    3660
gttccaagtt tggttcaaat cgagcgagct ggaggcaaca ggaaaagagg gcactaagcg    3720
gccgctaggg catgtctaga agtccgcaaa aatcaccagt ctctctctac aaatctatct    3780
ctctctattt ttctccagaa taatgtgtga gtagttccca gataagggaa ttagggttct    3840
tatagggttt cgctcatgtg ttgagcatat aagaaaccct tagtatgtat ttgtatttgt    3900
aaaatacttc tatcaataaa atttctaatt cctaaaacca aaatccagtg a              3951
```

<210> SEQ ID NO 3
<211> LENGTH: 8716
<212> TYPE: DNA
<213> ORGANISM: Artificial
<220> FEATURE:

<223> OTHER INFORMATION: synthesized, based on Arabidopsis and Choristoneura fumiferana

<400> SEQUENCE: 3

```
atagtttaaa ctgaaggcgg gaaacgacaa tctgatccaa gctcaagcta agcttgcatg     60
cctgcaggat atcgtggatc caagcttgcc acgtgccgcc acgtgccgcc acgtgccgcc    120
acgtgcctct agaggatcca tctccactga cgtaagggat gacgcacaat cccactatcc    180
ttcgcaagac ccttcctcta tataaggaag ttcatttcat ttggagagga cacgctggga    240
tccccaccat ggcccccccg accgatgtca gcctgggga cgaactccac ttagacggcg    300
aggacgtggc gatggcgcat gccgacgcgc tagacgattt cgatctggac atgttggggg    360
acggggattc cccaggtccg ggatttaccc cccacgactc cgccccctac ggcgctctgg    420
atatggccga cttcgagttt gagcagatgt ttaccgatgc ccttggaatt gacgagtacg    480
gtgggaagct tctaggtacc tccagaagaa tatcaggcgg ggaattcggc gggatgaagc    540
tactgtcttc tatcgaacaa gcatgcgata tttgccgact taaaaagctc aagtgctcca    600
aagaaaaacc gaagtgcgcc aagtgtctga agaacaactg ggagtgtcgc tactctccca    660
aaaccaaaag gtctccgctg actagggcac atctgacaga agtggaatca aggctagaaa    720
gactggaaca gctatttcta ctgatttttc ctcgagaaga ccttgacatg attttgaaaa    780
tggattcttt acaggatata aaagcattgt taacaggatt atttgtacaa gataatgtga    840
ataaagatgc cgtcacagat agattggctt cagtggagac tgatatgcct ctaacattga    900
gacagcatag aataagtgcg acatcatcat cggaagagag tagtaacaaa ggtcaaagac    960
agttgactgt atcgggaggc ggtgggatcc ggcctgagtg cgtagtaccc gagactcagt   1020
gcgccatgaa gcggaaagag aagaaagcac agaaggagaa ggacaaactg cctgtcagca   1080
cgacgacggt ggacgaccac atgccgccca ttatgcagtg tgaacctcca cctcctgaag   1140
cagcaaggat tcacgaagtg gtcccaaggt ttctctccga caagctgttg gtgacaaacc   1200
ggcagaaaaa catcccccag ttgacagcca accagcagtt ccttatcgcc aggctcatct   1260
ggtaccagga cgggtacgag cagccttctg atgaagattt gaagaggatt acgcagacgt   1320
ggcagcaagc ggacgatgaa aacgaagagt cggacactcc cttccgccag atcacagaga   1380
tgactatcct cacggtccaa cttatcgtgg agttcgcgaa gggattgcca gggttcgcca   1440
agatctcgca gcctgatcaa attacgctgc ttaaggcttg ctcaagtgag gtaatgatgc   1500
tccgagtcgc gcgacgatac gatgcggcct ccgacagtgt tctgttcgcg aacaaccaag   1560
cgtacactcg cgacaactac cgcaaggctg gcatggccta cgtcatcgag gatctactgc   1620
acttctgccg gtgcatgtac tctatggcgt tggacaacat ccattacgcg ctgctcacgg   1680
ctgtcgtcat cttttctgac cggccagggt tggagcagcc gcaactggtg gaagagatcc   1740
agcggtacta cctgaatacg ctccgcatct atatcctgaa ccagctgagc gggtcggcgc   1800
gttcgtccgt catatacggc aagatcctct caatcctctc tgagctacgc acgctcggca   1860
tgcaaaactc caacatgtgc atctccctca agctcaagaa cagaaagctg ccgcctttcc   1920
tcgaggagat ctgggatgtg gcggacatgt cgcacaccca accgccgcct atcctcgagt   1980
cccccacgaa tctctagccc ctgcgcgcac gcatcgccga tgccgcgtcc ggccgcgctg   2040
ctctgagaat tcgatatcaa gcttctagac ccgggctgca gagatctacg cgttaagctt   2100
aattcccgat cgttcaaaca tttggcaata aagtttctta agattgaatc ctgttgccgg   2160
tcttgcgatg attatcatat aatttctgtt gaattacgtt aagcatgtaa taattaacat   2220
```

```
gtaatgcatg acgttatttta tgagatgggt ttttatgatt agagtcccgc aattatacat    2280
ttaatacgcg atagaaaaca aaatatagcg cgcaaactag gataaattat cgcgcgcggt    2340
gtcatctatg ttactagatc ggggactagt aaggccggcc gcttggatcc gctcggagga    2400
cagtactccg ctcggaggac agtactccgc tcggaggaca gtactccgct cgaggacagt    2460
actccgctcg gaggacagta ctccgatccg tcagatctgc aagacccttc ctctatataa    2520
ggaagttcat ttcatttgga gaggacacgc tgaaccatga cgataccgga tctctgtaac    2580
gatttggtcg atgagatact ctgtcgcgtt ccggcgagga atctgaaacg gttacgatct    2640
accagcaaac gatggaaccg tttattcaaa gatgatagga gattcgcaag agagcacatg    2700
cataaagccc caaggagta tctacctctc atgttgacaa gcgagtacag gatctgtccg    2760
gtgagcatca atctccaagg agatgttcct tctgtagtgt taaagagaga gcttagccta    2820
ccagatccgg attattcaca tcaattcgat ataggtcgag tctttcactg cgacggctta    2880
ttggtatgca accacgtagg caagaatccc cgatacggat ctaaaatcgt ggtttggaac    2940
ccgctgactg gtcaaaccag gtggatcgaa gccggctatc gttggaagga atacgaagtc    3000
agatttgttc tcggatactg ctaccagcaa gacgagaaca attcctgcag taaaaaaatc    3060
tacaaaattt tgtgttttta tcctaatggc caagatacag aaatctacga gcttaactac    3120
tctgataggt ggacaaggac gattcctgat ggtgatctca ctccaggctg gaccttgata    3180
tactcagagc agaccgtgtc tatgaatgga aatctttact tgtttgcttc ggagaaatca    3240
aaacccatc ttggcgtgtc cttgctcaga tttgatttct caacagagaa atcatctcta    3300
tgtgtgactc ttccctatca gcgtccaagg tatgaaattt tgagtatttc cgccgttaga    3360
ggaggagaga atctttctct gttgttgcag ctcgattttg aatctaagac tgagatatgg    3420
gtgacgaata agattgatga caccaccacc aaaggagcag cagtctcttg gaccaaggtc    3480
ctagcatttg atttaagccc tgatcttcaa ttattttcgg aggaggtaaa ttttttgctt    3540
gacgaggata agaaagtcgc tgtgtgttgt gagagatggt tggaaccgca agagcaccac    3600
aggtaccagt gcaggagaga gtacaagatc accgacaaga tatacattct cggggaggat    3660
aataaagtcg atgaagtagg ttctggagag ggagaggcta cagattcact tgaaggaatt    3720
tcgcaagtta ttctcaatta cgctccaagt ttggtccaaa tcgagcaagc cggaggaggc    3780
aaaacaaaaa gaggtgacga ctaagcggcc gctagggcat gtctagaagt ccgcaaaaat    3840
caccagtctc tctctacaaa tctatctctc tctattttc tccagaataa tgtgtgagta    3900
gttcccagat aagggaatta gggttcttat agggtttcgc tcatgtgttg agcatataag    3960
aaacccttag tatgtatttg tatttgtaaa atacttctat caataaaatt tctaattcct    4020
aaaaccaaaa tccagtgact gcaggcatgc aagcttatcg ataccgtcga cgattgatgc    4080
atgttgtcaa tcaattggca agtcataaaa tgcattaaaa aatatttttca tactcaacta    4140
caaatccatg agtataacta aattataaa gcaatgatta gaatctgaca aggattctgg    4200
aaaattacat aaaggaaagt tcataaatgt ctaaaacaca agaggacata cttgtattca    4260
gtaacatttg cagcttttct aggtctgaaa atatatttgt tgcctagtga ataagcataa    4320
tggtacaact acaagtgttt tactcctcat attaacttcg gtcattagag ccacgatttt    4380
gacacatttt tactcaaaac aaaatgtttg catatctctt ataatttcaa attcaacaca    4440
caacaaataa gagaaaaaac aaataatatt aatttgagaa tgaacaaaag gaccatatca    4500
ttcattaact cttctccatc catttccatt tcacagttcg atagcgaaaa ccgaataaaa    4560
aacacagtaa attacaagca caacaaatgg tacaagaaaa acagtttttcc caatgccata    4620
```

```
atactcaaac tcagtaggat tctggtgtgt gcgcaatgaa actgatgcat tgaacttgac    4680
gaacgttgtc gaaaccgatg atacgaacga aagctctaga ggatcaattc gagctcttag    4740
gtcgacccac gtttgccaaa accaactcct gctctccttt tttgtcgtgc ttctactctt    4800
tcagggcttg gcaatccagt ttttt cttcg tacttctttt ctagggcctc tagctcttca    4860
cgaatgctat caagaacttg atccgtcatt ctgtcaaaga agagaactcc ctccagatgg    4920
tcgtattcgt gctgaaagat tcgtgcaggt aaacgtgata gactgattga aaatctttca    4980
ccagtaatat cccttgcatc aatcttgaca gattgtggtc gaacaacttc agcatagatc    5040
cccgggaagg agaggcatcc ttcatcaaac ggtactaatt tatcggaata tttcttgatt    5100
ttcggattta caaggacaat ttcttttcct tctccaggct ctccagctgg attaaacacc    5160
atgagttgaa cattgagacc tacttgtggt gctgagagcc caatgccatc cgttttgtac    5220
ataacatcaa acatagcatc aaccaagttc tttaaattct cgtcaaaaat atcaatcctc    5280
ttgttcttag cccgtagtat aggatccgga tactcaacaa tcttcaaagg cgtctcaaat    5340
tgaacatcag tagctgaagc tactttatcg tctttacgcg agacgcgctt tacttctgcg    5400
cggaccgaag atgtcagagg actggtccgg ttcacagtag agcagaacgt gaccgtggat    5460
ttgagccgac cataaccggc agagagagta gtagctcggc gagataaaac cggtaggagt    5520
atgcgagaga gtggtggagc ttggaggaag cagttacaga cggctcccat ggtgaagta     5580 tttgaaagaa aattaaaaat aaaaagatcc gctcgaggat ccaagcttag atgagagatt    5640
tcgattccga ttttgatttc gattccgatt tgatttcga ttgatctctt ccttctgatt     5700
tgtgttcctt atataaggaa attcttgtgg gattagacgt catggcttac gtcatttcct    5760
tcgtcctgtt gctcactgat tgagctgtga gtggagggac cactggaaga tgcttcacta    5820
attttcttag tggagggacc ggcttcacat gcttcacaca agtggctgtc gggcatcatc    5880 tttttagct tttgacaaag caatgtttta gtggtggctc ccactcttat cttcaacatt      5940
attatcttat cttcaaagga cgataagatg ttgatgtctg tggacgaagt tgggattaga    6000
cgtcatggct tacgtcattt ccttcgtcct gttgctcact gattgagctg tgagtggagg    6060
gaccactgga agatgcttca ctaatttct tagtggaggg accggcttct catgcttcac     6120
acaagtggct gtcgggcatc atcttttttta gcttttgaca aagcaatgtt ttagtggggg    6180
ctcccactct tatcttcaac attattatct tatcttcaaa ggacgataag atgttgatgt    6240
ctgtggacga agttgacgaa tttcgacctg caggcatgca agcttggcgt aatcatggtc    6300
atagctgttt cctgtgtgaa attgttatcc gctcacaatt ccacacaaca tacgagccgg    6360
aagcataaag tgtaaagcct ggggtgccta atgagtgagc taactcacat taattgcgtt    6420
gcgctcactg cccgctttcc agtcgggaaa cctgtcgtgc cagctgcatt aatgaatcgg    6480
ccaacgcgcg gggagaggcg gtttgcgtat tgggccaaag acaaagggc gacattcaac     6540 cgattgaggg agggaaggta aatattgacg gaaattattc attaaaggtg aattatcacc    6600
gtcaccgact tgagccattt gggaattaga gccagcaaaa tcaccagtag caccattacc    6660
attagcaagg ccggaaacgt caccaatgaa accatcgata gcagcaccgt aatcagtagc    6720
gacagaatca agtttgcctt tagcgtcaga ctgtagcgcg ttttcatcgg cattttcggt    6780
catagccccc ttattagcgt ttgccatctt ttcataatca aaatcaccgg aaccagagcc    6840
accaccggaa ccgcctccct cagagccgcc accctcagaa ccgccaccct cagagccacc    6900
accctcagag ccgccaccag aaccaccacc agagccgccg ccagcattga caggaggccc    6960
```

-continued

```
gatctagtaa catagatgac accgcgcgcg ataatttatc ctagtttgcg cgctatattt   7020
tgttttctat cgcgtattaa atgtataatt gcgggactct aatcataaaa acccatctca   7080
taaataacgt catgcattac atgttaatta ttacatgctt aacgtaattc aacagaaatt   7140
atatgataat catcgcaaga ccggcaacag gattcaatct taagaaactt tattgccaaa   7200
tgtttgaacg atcggggatc atccgggtct gtggcgggaa ctccacgaaa atatccgaac   7260
gcagcaagat atcgcggtgc atctcggtct tgcctgggca gtcgccgccg acgccgttga   7320
tgtggacgcc gggcccgatc atattgtcgc tcaggatcgt ggcgttgtgc ttgtcggccg   7380
ttgctgtcgt aatgatatcg gcaccttcga ccgcctgttc cgcagagatc ccgtgggcga   7440
agaactccag catgagatcc ccgcgctgga ggatcatcca gccggcgtcc cggaaaacga   7500
ttccgaagcc caacctttca tagaaggcgg cggtggaatc gaaatctcgt gatggcaggt   7560
tgggcgtcgc ttggtcggtc atttcgaacc ccagagtccc gctcagaaga actcgtcaag   7620
aaggcgatag aaggcgatgc gctgcgaatc gggagcggcg ataccgtaaa gcacgaggaa   7680
gcggtcagcc cattcgccgc caagctcttc agcaatatca cgggtagcca acgctatgtc   7740
ctgatagcgg tccgccacac ccagccggcc acagtcgatg aatccagaaa agcggccatt   7800
ttccaccatg atattcggca agcaggcatc gccatgggtc acgacgagat catcgccgtc   7860
gggcatgcgc gccttgagcc tggcgaacag ttcggctggc gcgagcccct gatgctcttc   7920
gtccagatca tcctgatcga caagaccggc ttccatccga gtacgtgctc gctcgatgcg   7980
atgtttcgct tggtggtcga atgggcaggt agccggatca agcgtatgca gccgccgcat   8040
tgcatcagcc atgatggata ctttctcggc aggagcaagg tgagatgaca ggagatcctg   8100
ccccggcact tcgcccaata gcagccagtc ccttcccgct tcagtgacaa cgtcgagcac   8160
agctgcgcaa ggaacgcccg tcgtggccag ccacgatagc cgcgctgcct cgtcctgcag   8220
ttcattcagg gcaccggaca ggtcggtctt gacaaaaaga accgggcgcc cctgcgctga   8280
cagccggaac acggcggcat cagagcagcc gattgtctgt tgtgcccagt catagccgaa   8340
tagcctctcc acccaagcgg ccggagaacc tgcgtgcaat ccatcttgtt caatcatgcg   8400
aaacgatcca gatccggtgc agattatttg gattgagagt gaatatgaga ctctaattgg   8460
ataccgaggg gaatttatgg aacgtcagtg gagcattttt gacaagaaat atttgctagc   8520
tgatagtgac cttaggcgac ttttgaacgc gcaataatgg tttctgacgt atgtgcttag   8580
ctcattaaac tccagaaacc cgcggctgag tggctccttc aacgttgcgg ttctgtcagt   8640
tccaaacgta aaacggcttg tcccgcgtca tcggcggggg tcataacgtg actcccttaa   8700
ttctccgctc atgatc                                                   8716
```

```

<210> SEQ ID NO 4
<211> LENGTH: 8629
<212> TYPE: DNA
<213> ORGANISM: Artificial
<220> FEATURE:
<223> OTHER INFORMATION: synthesized, based on Arabidopsis and
      Choristoneura fumiferana

<400> SEQUENCE: 4
atagtttaaa ctgaaggcgg gaaacgacaa tctgatccaa gctcaagcta agcttgcatg     60
cctgcaggat atcgtggatc caagcttgcc acgtgccgcc acgtgccgcc acgtgccgcc    120
acgtgcctct agaggatcca tctccactga cgtaagggat gacgcacaat cccactatcc    180
ttcgcaagac ccttcctcta tataaggaag ttcatttcat ttggagagga cacgctggga    240
```

-continued

```
tccccaccat ggatccgcca ccatgctagc ccaccatgaa gctactgtct tctatcgaac    300
aagcatgcga tatttgccga cttaaaaagc tcaagtgctc caaagaaaaa ccgaagtgcg    360
ccaagtgtct gaagaacaac tgggagtgtc gctactctcc caaaaccaaa aggtctccgc    420
tgactagggc acatctgaca gaagtggaat caaggctaga aagactggaa cagctatttc    480
tactgatttt tcctcgagaa gaccttgaca tgattttgaa aatggattct ttacaggata    540
taaaagcatt gttaacagga ttatttgtac aagataatgt gaataaagat gccgtcacag    600
atagattggc ttcagtggag actgatatgc ctctaacatt gagacagcat agaataagtg    660
cgacatcatc atcggaagag agtagtaaca aaggtcaaag acagttgact gtatccatgg    720
ccccccccgac cgatgtcagc ctgggggacg aactccactt agacggcgag gacgtggcga    780
tggcgcatgc cgacgcgcta gacgatttcg atctggacat gttggggggac ggggattccc    840
caggtccggg atttaccccc cacgactccg ccccctacgg cgctctggat atggccgact    900
tcgagtttga gcagatgttt accgatgccc ttggaattga cgagtacggt gggaagcttc    960
taggtacctc tagaagaata tcgtggcctg agtgcgtagt acccgagact cagtgcgcca   1020
tgaagcggaa agagaagaaa gcacagaagg agaaggacaa actgcctgtc agcacgacga   1080
cggtggacga ccacatgccg cccattatgc agtgtgaacc tccacctcct gaagcagcaa   1140
ggattcacga agtggtccca aggtttctct ccgacaagct gttggagaca aaccggcaga   1200
aaaacatccc ccagttgaca gccaaccagc agttccttat cgccaggctc atctggtacc   1260
aggacgggta cgagcagcct tctgatgaag atttgaagag gattacgcag acgtggcagc   1320
aagcggacga tgaaaacgaa gagtcggaca ctccccttccg ccagatcaca gagatgacta   1380
tcctcacggt ccaacttatc gtggagttcg cgaagggatt gccagggttc gccaagatct   1440
cgcagcctga tcaaattacg ctgcttaagg cttgctcaag tgaggtaatg atgctccgag   1500
tcgcgcgacg atacgatgcg gcctccgaca gtgttctgtt cgcgaacaac caagcgtaca   1560
ctcgcgacaa ctaccgcaag gctggcatgg cctacgtcat cgaggatcta ctgcacttct   1620
gccggtgcat gtactctatg gcgttggaca acatccatta cgcgctgctc acggctgtcg   1680
tcatcttttc tgaccggcca gggttggagc agccgcaact ggtggaagag atccagcggt   1740
actacctgaa tacgctccgc atctatatcc tgaaccagct gagcgggtcg cgcgcgttcgt   1800
ccgtcatata cggcaagatc ctctcaatcc tctctgagct acgcacgctc ggcatgcaaa   1860
actccaacat gtgcatctcc ctcaagctca agaacagaaa gctgccgcct ttcctcgagg   1920
agatctggga tgtggcggac atgtcgcaca cccaaccgcc gcctatcctc gagtcccccca   1980
cgaatctcta gccccctgcgc gcacgcatcg ccgatgccgc gtccggccgc gctgctctga   2040
gaattcgata tcaagcttct agacccgggc tgcagagatc tacgcgttaa gcttaattcc   2100
cgatcgttca aacatttggc aataaagttt cttaagattg aatcctgttg ccggtcttgc   2160
gatgattatc atataatttc tgttgaatta cgttaagcat gtaataatta acatgtaatg   2220
catgacgtta tttatgagat gggttttat gattagagtc ccgcaattat acatttaata   2280
cgcgatagaa acaaaatat agcgcgcaaa ctaggataaa ttatcgcgcg cggtgtcatc   2340
tatgttacta gatcggggac tagtaaggcc ggccgcttgg atccgctcgg aggacagtac   2400
tccgctcgga ggacagtact ccgctcgag gacagtactc cgctcgagga cagtactccg   2460
ctcggaggac agtactccga tccgtcagat ctgcaagacc cttcctctat ataaggaagt   2520
tcatttcatt tggagaggac acgctgaacc atgaagacaa tacaggagca gcttccaaat   2580
gacttggtag aggagatact ctgtcgcgtt ccggcaacat ctctgagacg tttacgatcg   2640
```

```
acttgcaaag catggaaccg tttattcaaa ggtgatcgga tattagcaag taagcatttt    2700
gaaaaatccg caaaacagtt tagatctcta tcgttaagga atgattacag gattttccg     2760 attagcttca atctccatgg aaatagtcca tctctagagc ttaaaagtga gctaatcgat    2820
cctcattcta agaattcagc tgctccattc gaaatatctc gagtcattca ctgtgaggga   2880
ttgttgttgt gctcctccca attggacgaa tctagagtcg tggtttggaa tcctttaacc    2940
ggtgaaacca ggtggatcag aaccggcgat tttcgccaaa aaggccgtag ctttgatgtc    3000
gggtactact accaaaaaga caagagatcc tggatcaaga gctacaaact cttgtgctat    3060
tatcgtggta ccaaatattt tgaaatctac gattttgact ctgattcatg gaggattctt    3120
gatgatatta tcgctccacg ggggagtatt ggatactcgg aacttagcgt gtctctgaaa    3180
ggaaatactt actggttcgc taaaggtgta acagaagagc ggccccgcac catatcattg    3240
ctcaaatttg atttttatac agagaaatct gtacctgtgc ttcttcccta tcagagtcgt    3300
cgtcttttcc aagctagtag cctttctgtt gttagagaag ataaactttc tgtgttattg    3360
cagctagatc aaagttccaa gactgagata tgggtgacaa atgtgattga tgagaccacc    3420
aaaggagcag tttcttggac caaggtctta gcattggatt tgagccctca tcttcagatt    3480
gggaatgatg gaagtttctt cctaggcgag gataagaaag tcgtcatgtt ctgtgagaaa    3540
ttgattgatg agaacaaggt caaagacatg gtctacattg ttggggagga taatgttgtc    3600
acagaagtgg gatttggagt agatgaaatg gatggatgtc gggcagttat tcttaattat    3660
gttccaagtt tggttcaaat cgagcgagct ggaggcaaca ggaaaagagg gcactaagcg    3720
gccgctaggg catgtctaga agtccgcaaa aatcaccagt ctctctctac aaatctatct    3780
ctctctattt ttctccagaa taatgtgtga gtagttccca gataagggaa ttagggttct    3840
tatagggttt cgctcatgtg ttgagcatat aagaaaccct tagtatgtat ttgtatttgt    3900
aaaatacttc tatcaataaa atttctaatt cctaaaacca aaatccagtg actgcaggca    3960
tgcaagctta tcgataccgt cgacgattga tgcatgttgt caatcaattg gcaagtcata    4020
aaatgcatta aaaatatttt tcatactcaa ctacaaatcc atgagtataa ctataattat    4080
aaagcaatga ttagaatctg acaaggattc tggaaaatta cataaggaa agttcataaa     4140 tgtctaaaac acaagaggac atacttgtat tcagtaacat ttgcagcttt tctaggtctg    4200
aaaatatatt tgttgcctag tgaataagca taatggtaca actacaagtg ttttactcct    4260
catattaact tcggtcatta gaggccacga tttgacacat ttttactcaa aacaaaatgt    4320
ttgcatatct cttataattt caattcaac acacaacaaa taagagaaaa aacaaataat     4380
attaatttga gaatgaacaa aaggaccata tcattcatta actcttctcc atccatttcc    4440
atttcacagt tcgatagcga aaaccgaata aaaaacacag taaattacaa gcacaacaaa    4500
tggtacaaga aaaacagttt tcccaatgcc ataatactca aactcagtag gattctggtg    4560
tgtgcgcaat gaaactgatg cattgaactt gacgaacgtt gtcgaaaccg atgatacgaa    4620
cgaaagctct agaggatcaa ttcgagctct aggtcgacc cacgtttgcc aaaaccaact    4680
cctgctctcc ttttttgtcg tgcttctact ctttcagggc ttggcaatcc agttttttct    4740
tcgtacttct tttctagggc ctctagctct tcacgaatgc tatcaagaac ttgatccgtc    4800
attctgtcaa agaagagaac tccctccaga tggtcgtatt cgtgctgaaa gattcgtgca    4860
ggtaaacgtg atagactgat tgaaaatctt tcaccagtaa tatcccttgc atcaatcttg    4920
acagattgtg gtcgaacaac ttcagcatag atccccggga aggagaggca tccttcatca    4980
```

```
aacggtacta atttatcgga atatttcttg attttcggat ttacaaggac aatttctttt    5040
ccttctccag gctctccagc tggattaaac accatgagtt gaacattgag acctacttgt    5100
ggtgctgaga gcccaatgcc atccgttttg tacataacat caaacatagc atcaaccaag    5160
ttctttaaat tctcgtcaaa aatatcaatc ctcttgttct tagcccgtag tataggatcc    5220
ggatactcaa caatcttcaa aggcgtctca aattgaacat cagtagctga agctacttta    5280
tcgtctttac gcgagacgcg ctttacttct gcgcggaccg aagatgtcag aggactggtc    5340
cggttcacag tagagcagaa cgtgaccgtg gatttgagcc gaccataacc ggcagagaga    5400
gtagtagctc ggcgagataa aaccggtagg agtatgcgag agagtggtgg agcttggagg    5460
aagcagttac agacggctcc catggtggaa gtatttgaaa gaaaattaaa aataaaaaga    5520
tccgctcgag gatccaagct tagatgagag atttcgattc cgattttgat ttcgattccg    5580
attttgattt cgattgatct cttccttctg atttgtgttc cttatataag gaaattcttg    5640
tgggattaga cgtcatggct tacgtcattt ccttcgtcct gttgctcact gattgagctg    5700
tgagtggagg gaccactgga agatgcttca ctaattttct tagtggaggg accggcttca    5760
catgcttcac acaagtggct gtcgggcatc atctttttta gcttttgaca aagcaatgtt    5820
ttagtggtgg ctcccactct tatcttcaac attattatct tatcttcaaa ggacgataag    5880
atgttgatgt ctgtggacga agttgggatt agacgtcatg gcttacgtca tttccttcgt    5940
cctgttgctc actgattgag ctgtgagtgg agggaccact ggaagatgct tcactaattt    6000
tcttagtgga gggaccggct tctcatgctt cacacaagtg gctgtcgggc atcatctttt    6060
ttagcttttg acaaagcaat gttttagtgg gggctcccac tcttatcttc aacattatta    6120
tcttatcttc aaaggacgat aagatgttga tgtctgtgga cgaagttgac gaatttcgac    6180
ctgcaggcat gcaagcttgg cgtaatcatg gtcatagctg tttcctgtgt gaaattgtta    6240
tccgctcaca attccacaca acatacgagc cggaagcata aagtgtaaag cctggggtgc    6300
ctaatgagtg agctaactca cattaattgc gttgcgctca ctgcccgctt tccagtcggg    6360
aaacctgtcg tgccagctgc attaatgaat cggccaacgc gcggggagag gcggtttgcg    6420
tattgggcca agacaaaag gcgacattc aaccgattga gggagggaag gtaaatattg    6480
acggaaatta ttcattaaag gtgaattatc accgtcaccg acttgagcca tttgggaatt    6540
agagccagca aaatcaccag tagcaccatt accattagca aggccggaaa cgtcaccaat    6600
gaaaccatcg atagcagcac cgtaatcagt agcgacagaa tcaagtttgc ctttagcgtc    6660
agactgtagc gcgttttcat cggcattttc ggtcatagcc cccttattag cgtttgccat    6720
cttttcataa tcaaaatcac cggaaccaga gccaccaccg gaaccgcctc cctcagagcc    6780
gccaccctca gaaccgccac cctcagagcc accaccctca gagccgccac cagaaccacc    6840
accagagccg ccgccagcat tgacaggagg cccgatctag taacatagat gacaccgcgc    6900
gcgataattt atcctagttt gcgcgctata ttttgtttttc tatcgcgtat taaatgtata    6960
attgcgggac tctaatcata aaaacccatc tcataaataa cgtcatgcat tacatgttaa    7020
ttattacatg cttaacgtaa ttcaacagaa attatatgat aatcatcgca agaccggcaa    7080
caggattcaa tcttaagaaa ctttattgcc aaatgtttga acgatcgggg atcatccggg    7140
tctgtggcgg gaactccacg aaaatatccg aacgcagcaa gatatcgcgg tgcatctcgg    7200
tcttgcctgg gcagtcgccg ccgacgccgt tgatgtggac gccgggcccg atcatattgt    7260
cgctcaggat cgtggcgttg tgcttgtcgg ccgttgctgt cgtaatgata tcggcacctt    7320
cgaccgcctg ttccgcagag atcccgtggg cgaagaactc cagcatgaga tccccgcgct    7380
```

```
ggaggatcat ccagccggcg tcccggaaaa cgattccgaa gcccaacctt tcatagaagg    7440
cggcggtgga atcgaaatct cgtgatggca ggttgggcgt cgcttggtcg gtcatttcga    7500
accccagagt cccgctcaga agaactcgtc aagaaggcga tagaaggcga tgcgctgcga    7560
atcgggagcg gcgataccgt aaagcacgag gaagcggtca gcccattcgc cgccaagctc    7620
ttcagcaata tcacgggtag ccaacgctat gtcctgatag cggtccgcca cacccagccg    7680
gccacagtcg atgaatccag aaaagcggcc attttccacc atgatattcg gcaagcaggc    7740
atcgccatgg gtcacgacga gatcatcgcc gtcgggcatg cgcgccttga gcctggcgaa    7800
cagttcggct ggcgcgagcc cctgatgctc ttcgtccaga tcatcctgat cgacaagacc    7860
ggcttccatc cgagtacgtg ctcgctcgat gcgatgtttc gcttggtggt cgaatgggca    7920
ggtagccgga tcaagcgtat gcagccgccg cattgcatca gccatgatgg atactttctc    7980
ggcaggagca aggtgagatg acaggagatc ctgccccggc acttcgccca atagcagcca    8040
gtcccttccc gcttcagtga caacgtcgag cacagctgcg caaggaacgc ccgtcgtggc    8100
cagccacgat agccgcgctg cctcgtcctg cagttcattc agggcaccgg acaggtcggt    8160
cttgacaaaa agaaccgggc gcccctgcgc tgacagccgg aacacggcgg catcagagca    8220
gccgattgtc tgttgtgccc agtcatagcc gaatagcctc tccacccaag cggccggaga    8280
acctgcgtgc aatccatctt gttcaatcat gcgaaacgat ccagatccgg tgcagattat    8340
ttggattgag agtgaatatg agactctaat tggataccga ggggaattta tggaacgtca    8400
gtggagcatt tttgacaaga aatatttgct agctgatagt gaccttaggc gacttttgaa    8460
cgcgcaataa tggtttctga cgtatgtgct tagctcatta aactccagaa acccgcggct    8520
gagtggctcc ttcaacgttg cggttctgtc agttccaaac gtaaaacggc ttgtcccgcg    8580
tcatcggcgg gggtcataac gtgactccct taattctccg ctcatgatc                8629
```

<210> SEQ ID NO 5
<211> LENGTH: 21
<212> TYPE: DNA
<213> ORGANISM: Artificial
<220> FEATURE:
<223> OTHER INFORMATION: corn

<400> SEQUENCE: 5
gttgtagaag gacgcgatgg a                                               21

<210> SEQ ID NO 6
<211> LENGTH: 21
<212> TYPE: DNA
<213> ORGANISM: Artificial
<220> FEATURE:
<223> OTHER INFORMATION: corn

<400> SEQUENCE: 6
caggtacaag agcgtcatgc a                                               21

<210> SEQ ID NO 7
<211> LENGTH: 20
<212> TYPE: DNA
<213> ORGANISM: Artificial
<220> FEATURE:
<223> OTHER INFORMATION: corn

<400> SEQUENCE: 7
tcctgttccc gctgggctgc                                                 20

```
<210> SEQ ID NO 8
<211> LENGTH: 24
<212> TYPE: DNA
<213> ORGANISM: Artificial
<220> FEATURE:
<223> OTHER INFORMATION: isolated from an adnovirus

<400> SEQUENCE: 8
tatataatgg atccccgggt accg                                          24

<210> SEQ ID NO 9
<211> LENGTH: 20
<212> TYPE: DNA
<213> ORGANISM: Artificial
<220> FEATURE:
<223> OTHER INFORMATION: Corn

<400> SEQUENCE: 9
cgtccctgcc ctttgtacac                                               20

<210> SEQ ID NO 10
<211> LENGTH: 21
<212> TYPE: DNA
<213> ORGANISM: Artificial
<220> FEATURE:
<223> OTHER INFORMATION: corn

<400> SEQUENCE: 10
acacttcacc ggaccattca a                                             21

<210> SEQ ID NO 11
<211> LENGTH: 19
<212> TYPE: DNA
<213> ORGANISM: Artificial
<220> FEATURE:
<223> OTHER INFORMATION: corn

<400> SEQUENCE: 11
ccgcccgtcg ctcctaccg                                                19
```

CONTROL OF TARGETED TURNOVER OF KEY ETHYLENE HORMONE SIGNALING PATHWAY PROTEINS TO MODULATE ETHYLENE SENSITIVITY IN PLANTS

BACKGROUND OF THE INVENTION

The phytohormone ethylene is a signaling molecule that regulates numerous physiological processes throughout the life cycle of plants, including responses during germination, flower and fruit development, as well as the response of the plants to a variety of environmental stressors, such as drought, heat, excessive salinity, and disease (see, e.g., Chen et al, 2005, Annals of Botany, 95:901-915; Czarny et al, 2006 Biotechnol. Adv., 24:410-419). Ethylene biosynthesis pathways and signaling/regulatory pathways and networks are well described. For example, see FIGS. 1 and 2 in Wang et al, "Ethylene Biosynthesis and Signaling Networks", in The Plant Cell, 2002 (Eds. American Society of Plant Biologists) pages S131-S151.

Several key steps in the ethylene signal transduction pathway are highly regulated in plants. For both EIN2 (ETHYLENE-INSENSITIVE2) and EIN3 (ETHYLENE INSENSITIVE3) proteins, their expression is induced by ethylene, which leads to an increased ethylene response. In addition, both EIN2 and EIN3 proteins are targeted for turnover by ETP1 (EIN2 TARGETING PROTEIN1) and ETP2 (EIN2 TARGETING PROTEIN2) or EBF1 (EIN3-BINDING F-BOX PROTEIN1) and EBF2 (EIN3-BINDING F-BOX PROTEIN2) respectively. The turnover of these key response signaling proteins helps to maintain plants in a repressed or "off" state in the absence of the hormone ethylene. Constitutive overexpression of ETP1 or ETP2 (Qiao et al., Genes Dev., 2009 Feb. 15; 23(4):512-21 (published on-line Feb. 4, 2009) or EBF1 or EBF2 (Guo and Ecker, 2003 Cell, 115:667-677) in transgenic *Arabidopsis* resulted in partial ethylene-insensitivity and reduced accumulation of EIN2 or EIN3 protein respectively.

Commercially, a common way to regulate ethylene response in plants, including fruits and vegetables and flowers, involves the application of a chemical to the plant, fruit, flower or vegetable, such as, for example 1-methylcyclopropene (1-MCP; AgroFresh, Inc.). 1-MCP is a compound that is used as a plant growth regulator that prevents ethylene from attaching to its receptors in plant tissues. Its application thereby increases the ethylene insensitivity of the plant. The temporary ablation of ethylene sensitivity can increase the plants' resistance or tolerance to stress, delay ripening, senescence, or flowering, among other commercially valuable manipulations of plant growth.

More recently, proposals to transform plant cells genetically with modified ethylene response receptors or other proteins involved in the ethylene response in plants have been suggested, such as in e.g., U.S. Pat. No. 6,294,716; US Patent Application Publication Nos. 2006/0200875, 2005/0066389, 2005/0060772 and 2004/0128719, among others. Such systems are directed to expression of a variety of mutated genes in the ethylene pathways. These systems generally employ a variety of suggested promoters to drive expression of the proteins, including constitutive promoters and tissue-specific promoters.

While the use of chemically regulated gene expression systems have been proposed for use in plants generally (M. Padidim, 2003 Curr. Opin Plant Biol., 6(2):169-77), many such systems are experimental only, or have been reported to have certain disadvantages. Among these disadvantages are the use of toxic or volatile inducers, low induction levels, poor translocation/movement in the plant, a slow ability to "turn-off" the expression of the gene or insufficient specificity to an inducer that is non-toxic to plants, among other issues. Such gene expression systems are not universally useful in all plants and selection of the operable components and their assembly is often challenging.

In the examples of the prior art, expression of the ethylene pathway genes is typically always on in all tissues and parts of the plant or is always on in specific tissues of the plant. However, tissue-specific promoters or low level constitutive promoters can be leaky or induced by an undesirable inducer. Such conventional promoters do not permit tight regulation of hormonal expression in the plant. The timing, duration and level of expression of the ethylene pathway genes are critical for normal physiological function. The induction of ethylene insensitivity at will and for a determined period of time has not been successfully demonstrated by the prior art.

There remains a need in the art for compositions and methods that permit controllable temporal regulation of ethylene sensitivity. This is particularly important for a gene product the expression of which is directly induced by the presence of ethylene. Such compositions and methods are needed for safe and effective use in agricultural crops and foodstuffs, as well as in other plants.

BRIEF DESCRIPTION OF THE DRAWINGS

FIGS. 3B-3I form a sequence map showing the components of p1004.

FIGS. 4B-4I form a sequence map showing the components of p1005.

SUMMARY OF THE INVENTION

Figure 1:
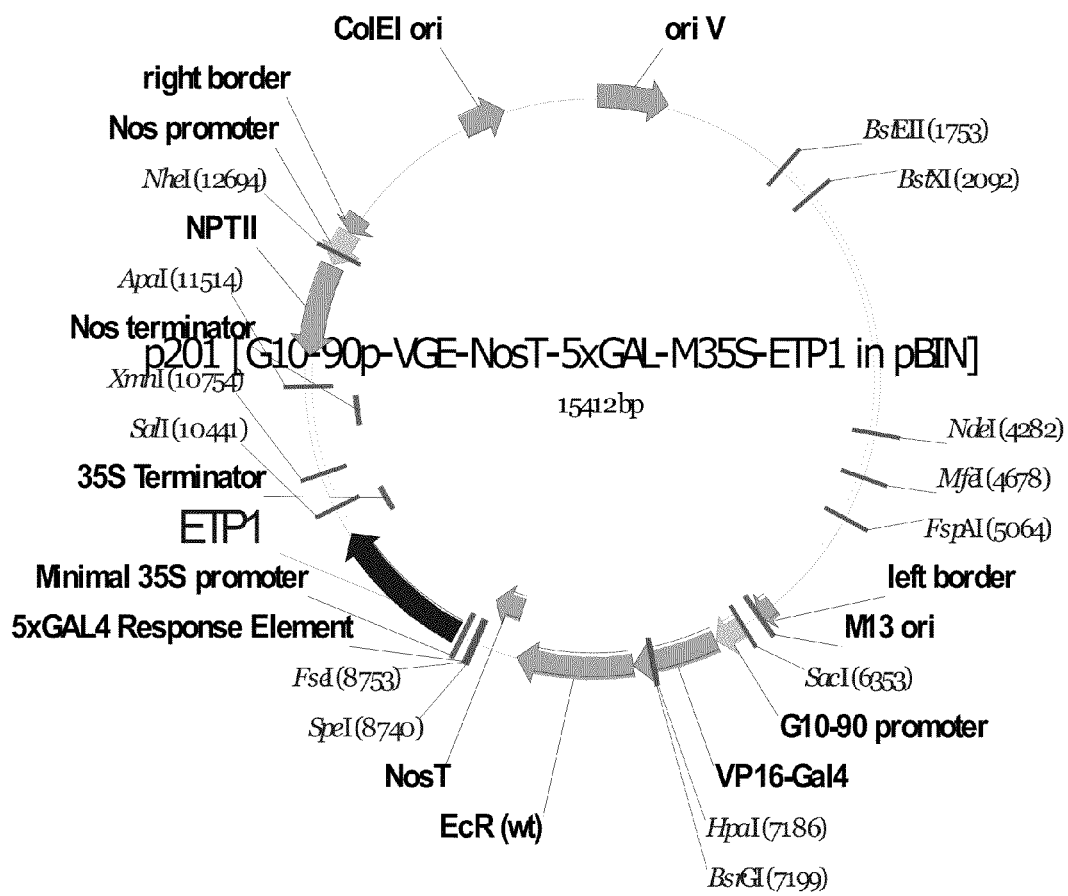
FIG. 1 is a schematic of an example of a plasmid designated p201 carrying both an activation cassette and a target cassette of the gene expression system (G10-90p-VGE-NosT-5xGAL-M35S-ETP1-35ST) with the components of the cassettes identified as disclosed in Example 1 and in SEQ ID NO: 1, and the cleavage sites identified by nucleic acid position in parentheses. The cassette portions of this plasmid are reported in SEQ ID NO: 1. The commercially available plasmid backbone is not provided in the sequence listing or figures, as it may be readily replaced with other plasmid backbones.

The compositions and methods described herein meet the need in the art by providing transgenic plants, plant cells, tissues, organs, fruits or flowers in which regulation of ethylene sensitivity may be reliably and safely controlled, e.g., in a temporal, qualitative and/or quantitative manner. These compositions and methods demonstrate tight regulation of gene expression, and thus hormonal expression, and are safe for use in agricultural crops and foodstuffs, as well as in other commercially valuable plants.

In one aspect, a gene expression system is provided for controllably inhibiting the accumulation in a plant cell of certain ethylene-inducible proteins. This system includes an activation cassette and a target cassette, which may be present on one or more plasmids. The activation cassette comprises a suitable promoter, a DNA-binding domain (DUD), an ecdysone receptor ligand binding domain (EcRLBD); and an activation domain (AD). The target cassette comprises a chemically inducible promoter (which can be a chemically-inducible tissue specific promoter) comprising, in operative association, the response element to which the DBD binds and a minimal promoter responsive to the AD. This chemically inducible promoter controls expression of a target nucleic acid sequence that encodes a selected regulatory protein or fragment thereof that upon expression operates to decrease the expression of the EIN2 or EIN3 gene product. Interaction among components of the two cassettes, when in the plant cell with an inducing composition, controllably increases expression of the regulatory protein and inhibits accumulation of the EIN2 or EIN3 gene product in the plant in the presence of ethylene. The inhibition of the accumulation of the EIN2 or EIN3 gene product is controllable by the timing, the concentration and the duration of the application of the inducing composition. The inducing composition may be absorbed by, and translocated within, the cells of the plant, where it interacts with the activation domain to turn on the chemically inducible promoter of the target cassette. Thus, this system permits controllable and selective modulation of ethylene sensitivity in the plant cell by expressing the regulatory protein at a sufficiently high level to overcome the plants' normal reaction to the presence of ethylene, i.e., which is to increase the expression of the ethylene-inducible protein, e.g., EIN2 or EIN3, which results in further activation of the downstream ethylene signal transduction pathway in a plant.

In another aspect, a plant cell is provided which expresses, stably or transiently, this above-described gene expression system.

In another aspect, a plant tissue or organ is provided which expresses, stably or transiently, this above-described gene expression system.

In another aspect, a transgenic plant is provided which expresses, stably or transiently, this above-described gene expression system.

In another aspect, a method for producing such a transgenic plant or portion thereof involves transforming at least one cell in the plant with the gene expression system described herein; generating a plant cell, tissue, organ or intact plant from the transformed plant cell; and selecting a plant cell, tissue, organ or intact plant which demonstrates the inhibition or decrease in accumulation of EIN2 or EIN3 when the plant cell, tissue, organ or intact plant is contacted with an inducing composition in the presence of ethylene. As stated above, the modulation in EIN2/EIN3 protein accumulation is controlled by the timing, the concentration, and the duration of the application of the inducing composition and the resulting increase in expression of the regulatory protein at sufficiently high levels. The inducing composition may be absorbed by and translocated within, the plant cell, tissue, organ or intact plant.

In a further aspect, a method for controlling ethylene sensitivity in a plant resulting from expression of ethylene-induced proteins, e.g., EIN2 or EIN3, involves applying an inducing composition to the cells of a transgenic plant or portion thereof, the plant comprising cells that stably or transiently express the gene expression system described herein. The inducing composition may be absorbed by, and translocated within, the plant cells. In the presence of the inducing composition, the response of the plant cells to ethylene, i.e., the normal increase in EIN2 or EIN3, and further downstream activation of the ethylene signal transduction pathway, is inhibited or decreased for a selected time; and the response of the plant cells to ethylene is increased after a selected time by depriving the plant of the inducer. This modulation in EIN2/EIN3 protein expression is controlled by the timing, the concentration, and the duration of the application of the inducing composition and its ability to express the regulatory protein at sufficiently high levels to make the plants ethylene insensitive. In one embodiment, the timing, concentration or duration of the inducing composition allows overexpression of the regulatory protein to decrease or inhibit the accumulation of an ethylene inducible signal protein in a plant cell in the presence of ethylene.

Other aspects and advantages of these methods and compositions are described further in the following detailed description.

DETAILED DESCRIPTION OF THE INVENTION

The compositions and methods described herein address the need in the art for compositions and methods for the controllable regulation of ethylene sensitivity in plants. More specifically, the compositions and methods described herein permit the deliberate variation of expression levels of ethylene-induced proteins, e.g., EIN2 or EIN3, based on use of selected amounts of a chemical inducer and the high level expression of the EIN2/EIN3 regulatory proteins (ETP1 and ETP2 or EBF1 and EBF2 respectively) to make the plants ethylene insensitive. Such an ability to manipulate hormonal regulation of the plants provides an agricultural benefit for the growth and ripening of crops, among other benefits described below.

The inventors have determined that the key to achieving practical ethylene insensitivity is dependent upon obtaining a sufficient level of the regulatory proteins that target the turnover of key ethylene-inducible, signal proteins in order to overcome the amount of the signal protein that is induced by ethylene. Making a plant insensitive to ethylene provides that plant with certain benefits, such as resistance to stress as discussed herein. However, ethylene sensitivity is required at certain times for the normal growth and development of plants. Thus the compositions and methods discussed herein are useful to precisely control the timing of when and the level of insensitivity of a plant to ethylene, and to be able to return that plant to a state of ethylene sensitivity in order to ensure the further normal growth and development of that plant.

I. GENE EXPRESSION SYSTEM

A gene expression or modulation system is employed for stable or transient expression in a plant cell. The components of such a system include at least two gene expression cassettes, each of which is capable of being expressed in a plant cell.

In one embodiment, the first gene expression cassette, referred to as the activation cassette, comprises a polynucleotide which is expressible in a plant cell encoding the following components under the control of a suitable promoter and in operative association therewith: (a) a DNA-binding domain (DBD) that recognizes a response element associated with a gene whose expression is to be modulated, i.e., a gene that encodes a regulatory protein, such as ETP1/ETP2 or EBF1/EBF2, that targets the turnover of a key ethylene-inducible, signal protein, e.g., EIN2 and EIN3, respectively; (b) a ligand binding domain (LBD) comprising an ecdysone receptor ligand binding domain (EcRLBD) or functional fragment thereof; and (c) an activation or transactivation domain (AD) which is activated in the presence of an inducing composition suitable for application to plants. In one embodiment, the components in the activation cassette are present in the following order 5' to 3': the LBD is downstream of the DBD, which is downstream of the AD. In another embodiment, the components in the activation cassette are present in the following order 5' to 3': the LBD is downstream of the AD, which is downstream of the DBD. In another embodiment, the components in the activation cassette are present in the following order 5' to 3': the DBD is downstream of the LBD, which is downstream of the AD. In another embodiment, the components in the activation cassette are present in the following order 5' to 3': the DBD is downstream of the AD, which is downstream of the LBD. In another embodiment, the components in the activation cassette are present in the following order 5' to 3': the AD is downstream of the LBD, which is downstream of the DBD. In another embodiment, the components in the activation cassette are present in the following order 5' to 3': the AD is downstream of the DBD, which is downstream of the LBD. The activation cassette also includes a terminator positioned preferable at the 3' terminus of the cassette. The specific identities of these components are discussed below.

The second gene expression cassette, i.e., the target cassette, comprises a polynucleotide encoding the following components. One component is a chemically inducible promoter comprising, in operative association, the response element (RE) to which the DBD of the protein encoded by the activation cassette binds and a minimal promoter responsive to the AD of the activation cassette. The other component is a target nucleic acid sequence that encodes a regulatory protein, such as ETP1/ETP2 or EBF1/EBF2, or a functional fragment of such a protein, that targets the turnover of a key ethylene-inducible, signal protein, e.g., EIN2 and EIN3, respectively. In one embodiment, the nucleic acid sequence is in sense orientation. The inducible promoter is in control of the expression of the selected regulatory protein-encoding sequence.

In another embodiment, the activation and/or target cassettes further comprise terminator sequences, such as downstream of the nucleic acid sequence encoding the protein sequence, and an optional selectable marker. Such markers are well-known and used for selecting cells that take up the genes in the presence of an antibiotic or other chemical. These optional components are discussed in more detail below.

This gene expression system operates so that the components of the activation cassette and the target cassette, when in the plant cell and in cooperation with an inducing composition, modulate expression of the selected regulatory protein. Modulation or regulation of the selected regulatory protein selectively modulates ethylene sensitivity in the plant cell. For example, one modulation involves increasing ethylene sensitivity of the plant cell by decreasing the expression of the regulatory protein. In another embodiment, the ethylene sensitivity of the plant cell is decreased by increasing the expression of the regulatory protein at a sufficiently high levels to overcome the competing normal reaction of the plant in the presence of ethylene, i.e., which operates normally to increase the expression and accumulate the gene product of the signal protein EIN2 or EIN3. This expression of the regulatory protein that modulates the ethylene pathway is controlled in the plant cell by the interaction of the components of the gene expression system with the inducing composition, particularly in the presence of ethylene. The inducing composition may be absorbed by, and/or translocated within, the cells of the plant.

The term "sufficiently high levels of expression" when referring to the expression levels of the regulatory protein that regulates the turnover of the signal proteins means an expression level that alters the response of a cell or plant to 10 ppm ethylene or 10 µM ACC (1-aminocyclopropane-1-carboxylic acid). In one embodiment, the expression level of the regulatory protein is high enough to overcome any increase in expression of the signal protein that normally results from the presence of ethylene or ACC. In another embodiment, the expression level of the regulatory protein is high enough to decrease expression of the signal protein in the presence of ethylene or ACC. In another embodiment, the expression level of the regulatory protein is high enough to overcome stress-induced ethylene production of the signal protein in a stressed plant, thus making the plant ethylene insensitive and overcoming the negative effects of the stress on the plant.

Figure 2:
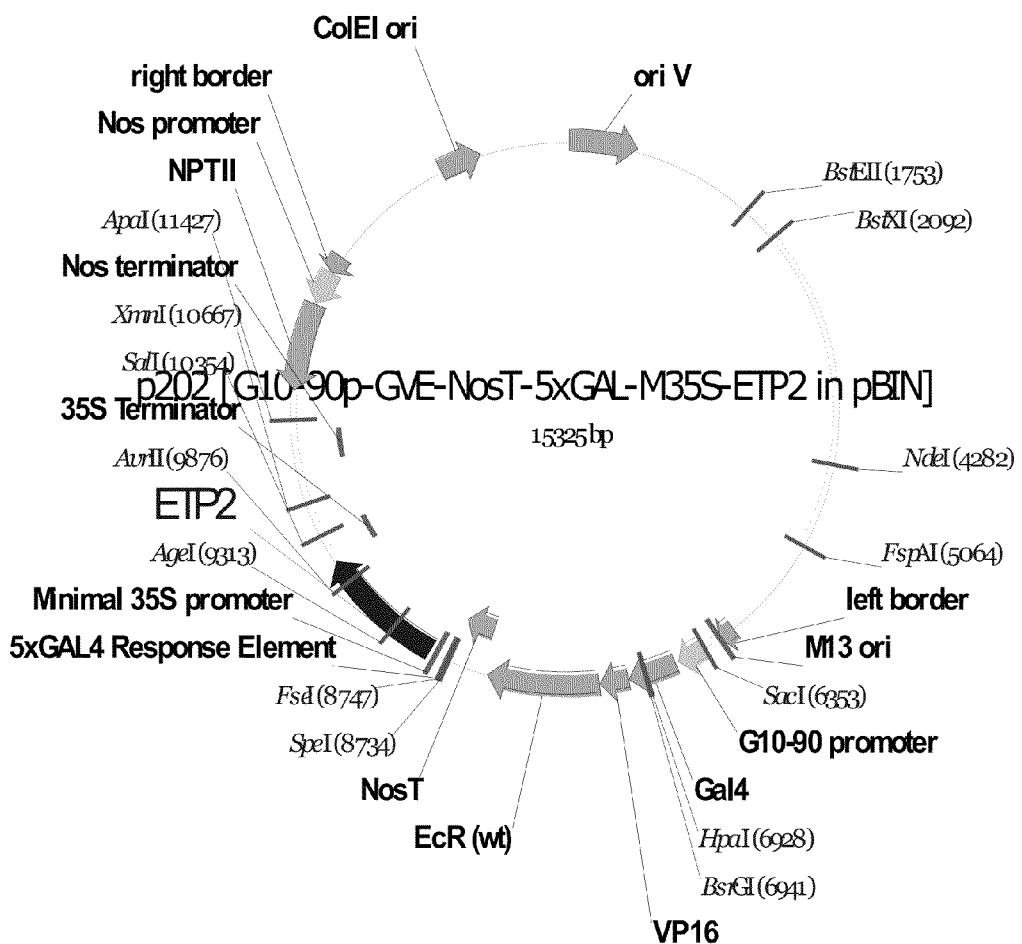
FIG. 2 is a schematic of an example of a plasmid designated p202, which contains both an activation cassette and target cassette (G10-90p-GVE-NosT-5xGAL-M35S-ETP2-35ST) for expression of ETP2 using GVE receptor-mediated inducible expression of ETP2. The cassette portions of this plasmid are reported in SEQ ID NO: 2. The commercially available plasmid backbone is not provided in the sequence listing or figures, as it may be readily replaced with other plasmid backbones.
Figure 3A:
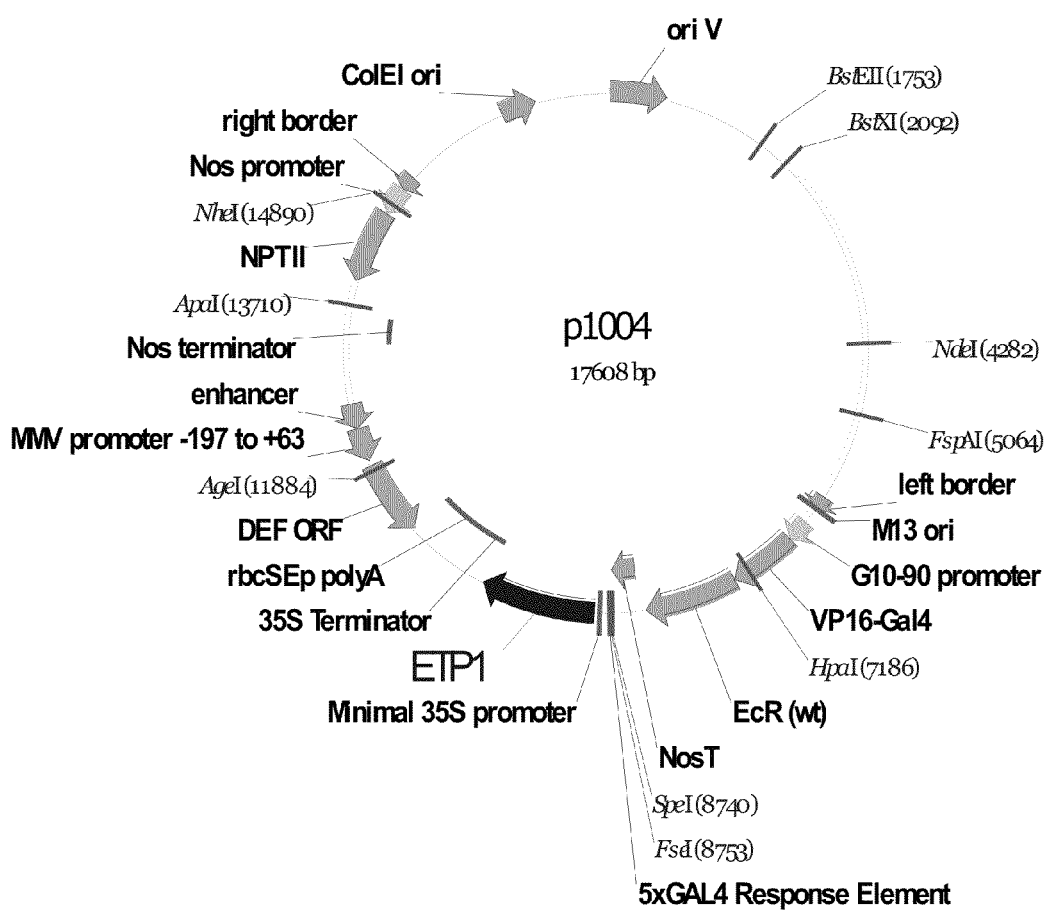
FIG. 3A is a schematic of an example of a plasmid designated p1004 [G10-90p-VGE-NosT-5xGAL-M35S-ETP1 and MMVp-def-rbcS-E9t] and its components are illustrated in SEQ ID NO: 3 and FIGS. 3B-3I, namely the G10-90 constitutive promoter, the VP16 activation domain and the GAL4 DNA binding domain, and the wildtype ecdysone receptor ligand binding domain associated with the NOS terminator sequence, the inducible promoter which consists of five copies of the GAL4 response element and the minimal 35S promoter, the ETP1 gene, the 35S terminator sequence, the MMV promoter, the P-DEF marker gene and the rbcS-E9 terminator.
Figure 4A:
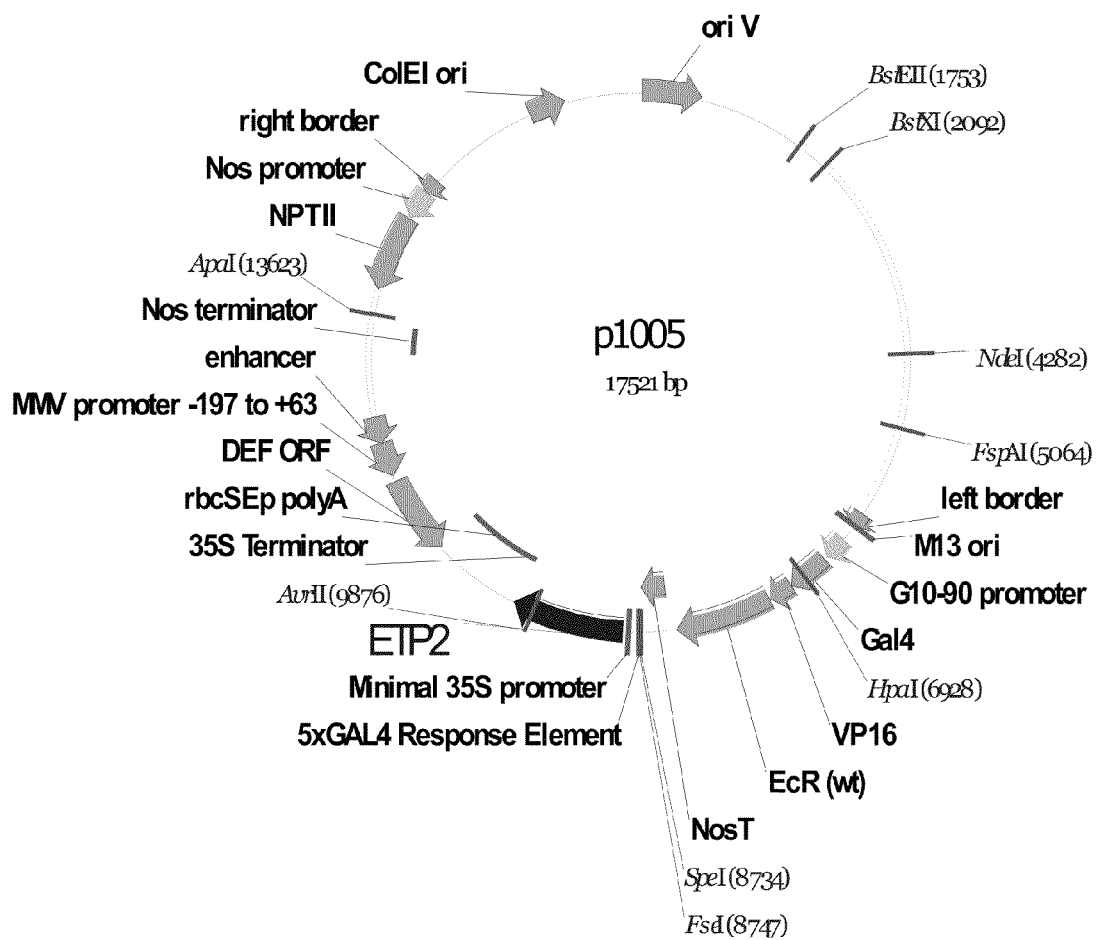
FIG. 4A is a schematic of an example of a plasmid designated p1005 [G10-90p-GVE-NosT-5xGAL-M35S-ETP2 and MMVp-def-rbcS-E9t] and its components are illustrated in SEQ ID NO: 4 and FIGS. 4B-4I, namely the G10-90 constitutive promoter, the GAL4 DNA binding domain, the VP16 activation domain, and the wildtype ecdysone receptor ligand binding domain described associated with the NOS terminator sequence, the inducible promoter which consists of five copies of the GAL4 response element and the minimal 35S promoter (nucleotide 2493 to 2548 of SEQ ID NO: 4), the ETP2 gene, the 35S terminator sequence, the MMV promoter, the P-DEF marker gene and the rbcS-E9 terminator.

In one embodiment of this system, the first cassette and second cassette are present on a single plasmid, such as that of FIGS. 1 and 2. In another embodiment, the first and second cassettes are present on separate plasmids.

In another embodiment of the gene expression system, a first gene expression cassette can contain a DBD and a first LBD; a second cassette can contain the AD and a second, different LBD; and a third cassette comprises a polynucleotide that encodes the response element to which the DBD of the first polypeptide binds, a promoter that is activated by the AD of the second cassette; and the target regulatory gene whose expression is to be modulated. In this system, the AD and DBD are operationally linked to two different proteins which in the presence of inducing composition activate the target gene expression. In one embodiment, the first LBD can be an EcR LBD, while the second LBD can be an LBD from a retinoid X receptor. In another embodiment, the second LBD can be an EcR LBD, while the first LBD can be an LBD from a retinoid X receptor. Such a construct is described in U.S. Pat. No. 7,091,038 or US patent publication No. US 2005/0266457, published Dec. 1, 2005.

The term "operably linked" or "operatively linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. In one embodiment, expression refers to translation of mRNA into a protein or polypeptide in another embodiment, the components of the gene expression system may be transiently expressed in the plant cell. In another embodiment, the components of the gene expression system may be stably expressed by integration into a chromosome of the plant cell. The selection of transient vs. stable integrated expression may be selected by one of skill in the art in generating and using the gene expression system as described herein.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation in the appropriate direction. These vectors or plasmids may optionally comprise a polynucleotide that encodes a polypeptide of interest and having elements in addition to the polynucleotide that facilitate transformation of a particular host cell. Such cassettes in certain embodiments also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

All other terms used herein employ the conventional meaning in the art, unless otherwise indicated. See, for example, the definition of the terms in U.S. Pat. No. 7,091,038.

A. The Promoter of the Activation Cassette

In one embodiment of the system, the promoter of the activation cassette is a nucleic acid sequence (DNA or RNA) that is capable of controlling the expression of the DBD, LBD and AD sequences within a transformed plant cell. In general, these three primary components of the activation cassette are located 3' to the selected promoter sequence. The promoter sequence consists of proximal and more distal upstream elements referred to as enhancers. An "enhancer" is a DNA sequence that can stimulate promoter activity and may be an innate element of the promoter or a heterologous element inserted to enhance the level or specificity of a promoter. Useful promoters in this context may be derived in their entirety from a native gene, or be composed of different elements derived from different promoters found in nature, or even comprise synthetic DNA segments.

In one embodiment, the promoter of the activation cassette is a constitutive promoter, e.g., a promoter that causes a gene to be expressed in most cell types at most times, so that the plant cell transformed with this cassette is continually producing the activation cassette components. For example, certain constitutive promoters that are useful in this activation cassette include, without limitation, the exemplified G10-90 promoter, the cauliflower mosaic virus 35S promoter, the *Cassava mosaic* virus promoter, the figwort mosaic virus promoter, the Badnavirus promoter, *Mirabilis mosaic* virus promoter, the Rubisco promoter, the Actin promoter, or the ubiquitin promoter.

In still other embodiments promoters that direct the expression of a gene in different tissues or cell types ("tissue specific", "cell specific" or "plant organ-specific promoters") may be used for this purpose. Desirably such promoters are native to or functional in plant tissues and plant cells, or mutant versions of promoters native to or functional in plant tissues and plant cells. However promoters for other tissues and cells from other sources, e.g., mammalian, invertebrate, etc, that operate in plant cells may also be employed for this purpose. Still other embodiments employ promoters that express the components at different stages of development ("developmentally-specific promoters" or "cell differentiation-specific promoter"), or in response to different environmental or physiological conditions. For an extensive list of tissue-specific promoters, see Gallie, US Patent Application Publication No. 2005/0066389, which describes seed-specific promoters derived from the following genes: MAC1 from maize (Sheridan, 1996 Genetics 142:1009-1020); Cat3 from maize (GenBank No. L05934, Abler 1993 Plant Mol. Biol. 22:10131-10138); vivparous-1 from *Arabidopsis* (Genbank No. U93215); atmyc1 from *Arabidopsis* (Urso, 1996 Plant Mol. Biol. 32:571-576; Conceicao 1994 Plant 5:493-505); napA and BnCysP1 from *Brassica napus* (GenBank No. J02798, Josefsson, 1987 JBL 26:12196-12201, Wan et al., 2002 Plant J 30:1-10); and the napin gene family from *Brassica napus* (Sjodahl, 1995 Planta 197:264-271). Fruit specific promoters include the promoter from the CYP78A9 gene (Ito and Meyerowitz, 2000 Plant Cell 12:1541-1550). Other tissue-specific promoters include the ovule-specific BEL1 gene described in Reiser, 1995 Cell 83:735-742, GenBank No. U39944; Ray, 1994 Proc. Natl. Acad. Sci. USA 91:5761-5765 and the egg and central cell specific FIE1 promoter. Sepal and petal specific promoters include the *Arabidopsis* floral homeotic gene APETALA1 (AP1) (Gustafson Brown, 1994 Cell 76:131-143; Mandel, 1992 Nature 360:273-277), a related promoter, for AP2 (see, e.g., Drews, 1991 Cell 65:991-1002; Bowman, 1991 Plant Cell 3:749-758). Another useful promoter is that controlling the expression of the unusual floral organs (ufo) gene of *Arabidopsis* (Bossinger, 1996 Development 122:1093-1102). Additional tissue specific promoters include a maize pollen specific promoter (Guerrero, 1990 Mol. Gen. Genet. 224:161-168); see also promoters described by Wakeley, 1998 Plant Mol. Biol. 37:187-192; Ficker, 1998 Mol. Gen. Genet. 257:132-142; Kulikauskas, 1997 Plant Mol. Biol. 34:809-814; Treacy, 1997 Plant Mol. Biol. 34:603-611). Useful promoters include those from the FUL gene (Mandel and Yanofsky, 1995 Plant Cell, 7:1763-1771) and promoters from the SHP1 and SHP2 genes (Flanagan et al. 1996 Plant J 10:343-353; Savidge et al., 1995 Plant Cell 7(6):721-733). Promoters may be derived from the TA29 gene (Goldberg et al., 1995 Philos Trans. R. Soc. Lond. B. Biol. Sci. 350:5-17).

Other suitable promoters include those from the gene encoding the 2S storage protein from *Brassica napus* (Dasgupta, 1993 Gene 133:301-302); the 2s seed storage protein gene family from *Arabidopsis*; the gene encoding oleosin 20 kD from *Brassica napus*, GenBank No. M63985; the genes encoding oleosin A, Genbank No. U09118, and, oleosin B, Genbank No. U09119, from soybean; the gene encoding oleosin from *Arabidopsis*, Genbank No. Z17657; the gene encoding oleosin 18 kD from maize, GenBank No. J05212 and Lee, 1994 Plant Mol. Biol. 26:1981-1987; and the gene encoding low molecular weight sulphur rich protein from soybean (Choi, 1995 Mol Gen, Genet. 246:266-268). The tissue specific E8 promoter from tomato and promoters from the ATHB-8, AtP1N1, AtPSK1 or TED3 genes (Baima et al., 2001 Plant Physiol. 126:643-655, Galaweiler et al., 1998 Science 282:2226-2230; Elge et al., 2001 Plant J. 26:561-571; Igarashi et al., 1998 Plant Mol. Biol. 36:917-927) are also useful.

A tomato promoter active during fruit ripening, senescence and abscission of leaves and, to a lesser extent, of flowers can be used (Blume, 1997 Plant J. 12:731-746). Other exemplary promoters include the pistil specific promoter in the potato (*Solanum tuberosum* L.) SK2 gene, encoding a pistil specific basic endochitinase (Fieker, 1997 Plant Mol. Biol. 35:425-431); the Blec4 gene from pea (*Pisum sativum* cv. Alaska), active in epidermal tissue of vegetative and floral shoot apices of transgenic alfalfa. A variety of promoters specifically active in vegetative tissues including promoters controlling patatin, the major storage protein of the potato tuber (e.g., Kim, 1994 Plant Mol. Biol. 26:603-615; and Martin, 1997 Plant J. 11:53-62), and the ORF13 promoter from *Agrobacterium rhizogenes* (Hansen, 1997 Mol. Gen. Genet. 254:337-343) can be used. Other useful vegetative tissue-specific promoters include: the tarin promoter of the gene encoding a globulin from a major taro (*Colocasia esculenta* L. Schott) corm protein family, tarin (Bezerra, 1995 Plant Mol. Biol. 28:137-144); the curculin promoter (de Castro, 1992 Plant Cell 4:1549-1559) and the promoter for the tobacco root specific gene TobRB7 (Yamamoto, 1991 Plant Cell 3:371-382). Leaf-specific promoters include the ribulose biphosphate carboxylase (RBCS) promoters, the tomato RBCS1, RBCS2 and RBCS3A genes (Meier, 1997 FEBS Lett. 415: 91-95). A ribulose bisphosphate carboxylase promoter expressed almost exclusively in mesophyll cells in leaf blades and leaf sheaths at high levels (Matsuoka, 1994 Plant J. 6:311-319), the light harvesting chlorophyll a/b binding protein gene promoter (Shiina, 1997 Plant Physiol. 115:477-483; Casal, 1998 Plant Physiol. 116:1533-1538), the *Arabidopsis thaliana* myb-related gene promoter (Atmyb5; Li, 1996 FEBS Lett. 379:117-121), and the Atmyb5 promoter (Busk, 1997 Plant J. 11:1285-1295) are useful promoters.

Useful vegetative tissue-specific promoters include meristematic (root tip and shoot apex) promoters, e.g., the "SHOOTMERISTEMLESS" and "SCARECROW" promoters (Di Laurenzio, 1996 Cell 86:423-433; and, Long, 1996 Nature 379:66-69. Another useful promoter controls the expression of 3-hydroxyl-3-methylglutaryl coenzyme A reductase HMG2 gene (see, e.g., Enjuto, 1995 Plant Cell. 7:517-527). Also useful are kn1 related genes from maize and other species which show meristem specific expression, see, e.g., Granger, 1996 Plant Mol. Biol. 31:373-378; Kerstetter, 1994 Plant Cell 6:1877-1887; Hake, 1995 Philos. Trans. R. Soc. Lond. B. Biol. Sci. 350:45-51, e.g., the *Arabidopsis thaliana* KNAT1 or KNAT2 promoters (see, e.g., Lincoln, 1994 Plant Cell 6:1859-1876).

In certain embodiments of the activation cassette, the promoters may be inducible or regulatable, e.g., causes expression of the nucleic acid sequence following exposure or treatment of the cell with an agent, biological molecule, chemical, ligand, light, or some other stimulus. A non-limiting list of such inducible promoters include the PR 1-a promoter, prokaryotic repressor-operator systems, and higher eukaryotic transcription activation systems, such as described in detail in U.S. Pat. No. 7,091,038. Such promoters include the tetracycline ("Tet") and lactose ("Lac") repressor-operator systems from *E. coli*. Other inducible promoters include the drought-inducible promoter of maize; the cold, drought, and high salt inducible promoter from potato, the senescence inducible promoter of *Arabidopsis*, SAG 12, and the embryogenesis related promoters of LEC1, LEC2, FUS3, AtSERK1, and AGL15, all known to those of skill in the art. Still other plant promoters which are inducible upon exposure to plant hormones, such as auxins or cytokinins, are useful in this context, as described in US Patent Application Publication No. US2005/0066389 and U.S. Pat. No. 6,294,716.

Essentially for the purposes of the activation cassette, any promoter capable of driving expression of the sequences of the DBD, LBD and AD is suitable, including but not limited to: viral promoters, bacterial promoters, plant promoters, synthetic promoters, constitutive promoters, tissue specific promoter, developmental specific promoters, inducible promoters, light regulated promoters; pathogenesis or disease related promoters, cauliflower mosaic virus 19S, cauliflower mosaic virus 35S, CMV 35S minimal, cassava vein mosaic virus (CsVMV), figwort mosaic virus, Badnavirus, *Mirabilis mosaic* virus, chlorophyll a/b binding protein, ribulose 1,5-bisphosphate carboxylase, shoot-specific, root specific, chitinase, stress inducible, rice tungro baciliform virus, plant super-promoter, potato leucine aminopeptidase, nitrate reductase, alcohol dehydrogenase, sucrose synthase, mannopine synthase, nopaline synthase, octopine synthase, ubiquitin, zein protein, actin and anthocyanin promoters In a preferred embodiment of the invention, the promoter is selected from the group consisting of a cauliflower mosaic virus 35S promoter, a cassava vein mosaic virus promoter, and a cauliflower mosaic virus 35S minimal promoter, a figwort mosaic virus promoter, a Badnavirus promoter, a *Mirabilis mosaic* virus, a ubiquitin (Ubc) promoter, and an actin promoter.

B. The DBD

As used herein, the term "DNA binding domain" comprises a minimal polypeptide sequence of a DNA binding protein, up to the entire length of a DNA binding protein, so long as the DNA binding domain functions to associate with a particular response element. The DNA binding domain binds, in the presence or absence of a ligand, to the DNA sequence of the RE to initiate or suppress transcription of downstream gene(s) under the regulation of this RE. In certain embodiments of the gene expression units, the DBD is located in the activation cassette, while the response element is located in the target cassette.

The DNA binding domain can be any DNA binding domain with a known response element, including synthetic and chimeric DNA binding domains, or analogs, combinations, or modifications thereof. In certain embodiments, the DBD is a GAL4 DBD, a LexA DBD, a transcription factor DBD, a Group H nuclear receptor member DBD, a steroid/thyroid hormone nuclear receptor superfamily member DBD, or a bacterial LacZ DBD. More preferably, the DBD is an insect ecdysone receptor DBD, a GAL4 DBD (see the sequence illustrated in the plasmids of the examples herein), or a LexA DBD. The sequences for such DBDs are publically available and described in publications such as U.S. Pat. No. 7,091,038 or US Patent Application Publication No. 2005/0266457. In other embodiments, the DBDs useful in this cassette include, without limitation, DNA binding domains obtained from the cI promoter, or lac promoter, which are also publically available sequences.

C. The Ecdysone LBD and Optional Second LBD

In certain embodiments of the gene expression system, the ecdysone receptor (EcR) LBD comprises all or a portion of an invertebrate ecdysone receptor or mutant thereof. EcR is a member of the nuclear steroid receptor super family that is characterized by signature DNA and ligand binding domains, and an activation domain (Koelle et al. 1991, Cell, 67:59 77; see also, U.S. Pat. No. 6,245,531 (Stanford). Ecdysone receptors are responsive to a number of steroidal compounds such as ponasterone A and muristerone A and non-steroidal compounds. EcR has five modular domains, A/B (transactivation), C (DNA binding, heterodimerization), D (Hinge, heterodimerization), E (ligand binding, heterodimerization and transactivation and F (transactivation) domains. Some of these domains such as A/B, C and E retain their function when they are fused to other proteins. Suitable portions of EcR for use as the LBD in the gene expression system described herein include domains D, E and F. For example, the sequence of the wildtype EcR LBD is present in SEQ ID NO: 1 at nucleotides 990 to 1997.

Preferably, the EcR is a Lepidopteran EcR, a Dipteran EcR, an Arthropod EcR, a Homopteran EcR and a Hemipteran EcR. More preferably, the EcR for use is a spruce budworm *Choristoneura fumiferana* EcR ("CfEcR"), a *Tenebrio molitor* EcR ("TmEcR"), a *Manduca sexta* EcR ("MsEcR"), a *Heliothies virescens* EcR ("HvEcR"), a silk moth *Bombyx mori* EcR ("BmEcR"), a fruit fly *Drosophila melanogaster* EcR ("DmEcR"), a mosquito *Aedes aegypti* EcR ("AaEcR"), a blowfly *Lucilia capitata* EcR ("LcEcR"), a Mediterranean fruit fly *Ceratitis capitata* EcR ("CcEcR"), a locust *Locusta migratoria* EcR ("LmEcR"), an aphid *Myzus persicae* EcR ("MpEcR"), a fiddler crab *Uca pugilator* EcR ("UpEcR"), an ixodid tick *Amblyomma americanum* EcR ("AmaEcR"), a white fly *Bamecia argentifoli* EcR ("BaEcR"), or a green leafhopper *Nephotetix cincticeps* EcR ("NcEcR"), among others. Even more preferably, the LBD is from spruce budworm (*Choristoneura fumiferana*) EcR ("CfEcR") or fruit fly *Drosophila melanogaster* EcR ("DmEcR").

Sequences for a variety of wildtype or mutant EcRs are publically available and described in such publications as, e.g., U.S. Pat. No. 7,091,038; International Patent Publication No. WO 97/38117 and U.S. Pat. Nos. 6,333,318, 6,265,173 and 5,880,333. While the examples below employ wildtype EcR sequences, it is expected that mutant sequences can be selected by one of skill in the art to perform in a similar manner. In one embodiment, for example, a mutant ecdysone receptor is one containing a mutation as described in the above cited US patent application publication No. 2005/0266457, e.g., a Group H nuclear receptor ligand binding domain comprising at least one mutation. In one embodiment, an ecdysone LBD that contains a mutation changing the codon ACA for Thr to a codon GTG for Val at the nucleotide positions equivalent to, e.g., 1374-1376, in SEQ ID NO: 2 would be a useful EcR LBD. This mutant EcR LBD is referred to as T52V and encodes a mutation of Thr to Val at amino acid position 335 in the full-length CfEcR. Still others of the EcR LBDs described in that publication may be useful in the gene expression system described herein. In another embodiment, the mutant ecdysone receptor LBD is that described in U.S. Pat. No. 6,245,531 (Stanford) or is a truncated EcR LBD sequence or a deletion mutant, among other mutant sequences known to the art. In another embodiment, the LBD is encoded by a polynucleotide that hybridizes to a known EcR LBD or mutant sequence under conventional hybridization conditions, such as a hybridization step in less than 500 mM salt and at least 37° C., and a washing step in 2×SSPE at least 63° C.

In certain embodiments the gene expression system employs a second LBD. The second LBD is not an ecdysone receptor polypeptide, but can be the ligand binding domain of a second nuclear receptor. Such second binding domains include, without limitation a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain. See, e.g., such binding domains described in US Patent Application Publication No. US 2005/0266457. Such LBDs are well known to those of skill in the art and are well described in the literature.

It is within the ability of one skilled in the art given the teachings herein and without undue experimentation to select one or more appropriate EcR LBD sequence and use it in place of the sequences exemplified below.

D. The Activation Domain

The activation or transactivation domain (abbreviated "AD") useful in the gene expression system may be any Group H nuclear receptor member AD, steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), a p65 transactivation domain (p65AD), a glucocorticoid activation domain or an analog, combination, or modification thereof. In a specific embodiment, the AD is a synthetic or chimeric AD, or is obtained from an EcR, a glucocorticoid receptor, VP16, GAL4, NF-κB, or B42 acidic activation domain AD. Preferably, the AD is an EcR AD, a VP16 AD, a B42 AD, or a p65 AD. Sequences for such activation domains are publically available in such publications as U.S. Pat. No. 7,091,038 or in other documents described herein. An exemplary VP16AD is described in plasmids described in the examples herein. Such domains are well known to those of skill in the art and are well described in the literature.

E. The "Inducible" Promoter System of the Target Cassette

In certain embodiments, the promoter of the target cassette is a multicomponent promoter sequence. It comprises a minimal promoter operatively associated with one or more copies of a response element corresponding to the DNA binding domain in the activation cassette.

A minimal promoter, as used herein, includes the core promoter (i.e., the sequence that mediates the initiation of transcription) and the 5' untranslated region (5'UTR) without enhancer sequences. Thus, for use in embodiments of the gene expression system, the minimal promoter may be a minimal promoter derived from any promoter described above in Part A for use in the activation cassette. In certain embodiments of target cassettes, desirable minimal promoters include: the cauliflower mosaic virus 35S minimal promoter; a synthetic E1b minimal promoter (SEQ ID NO: 8; see U.S. Pat. No. 7,091,038) and a synthetic TATA minimal promoter (TATATA; see US Patent Application Publication No. US 2005/0228016). Minimal promoters useful in the gene expression systems described herein may be readily selected by one of skill in the art from numerous promoters well described in the literature. The sequence of the 35S minimal promoter is described in the plasmids described in the examples below.

The other portion of the inducible promoter of the target cassette includes a response element ("RE") located 5' or 3' to the minimal promoter. One RE can have two different or identical minimal promoters on either side to express two different proteins. In one embodiment, the RE is operationally or operatively linked to the minimal promoter. A response element is one or more cis-acting DNA elements which confer responsiveness on a promoter mediated through interaction with the DNA-binding domains of the activation cassette. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. Examples of DNA sequences for response elements of the natural ecdysone receptor are described in Cherbas L. et al, 1991 Genes Dev. 5, 120 131; D'Avino P P. et al, 1995 Mol. Cell. Endocrinol, 113:19 and Antoniewski C. et al, 1994 Mol. Cell Biol. 14, 4465-4474, among other publications. The RE may be any response element corresponding to the DNA binding domain in the activation cassette, or an analog, combination, or modification thereof. A single RE may be employed or multiple REs, either multiple copies of the same RE or two or more different REs, may be used in target cassette. The RE can be modified or substituted with response elements for other DNA binding protein domains such as the GAL-4 protein from yeast (see Sadowski, et al. 1988 Nature, 335:563 564) or LexA protein from *E. coli* (see Brent and Ptashne 1985, Cell, 43:729 736), or synthetic response elements specific for targeted interactions with proteins designed, modified, and selected for such specific interactions (see, for example, Kim, et al. 1997 Proc. Natl. Acad. Sci., USA, 94:3616-3620) to accommodate chimeric receptors. In a specific embodiment, the RE is an RE from GAL4 ("GAL4RE"), preferably two or more copies. The examples below demonstrate the use of five copies of the GAL4 RE (i.e, 5×GAL4). However, other suitable RE include, without limitation, LexA, a Group H nuclear receptor RE, a steroid/thyroid hormone nuclear receptor RE, or a synthetic RE that recognizes a synthetic DNA binding domain. In other embodiments, the RE is an ecdysone response element (EcRE), or a LexA RE (operon, "op") comprising a polynucleotide sequence. All such RE are well described in the literature and may be readily selected by one of skill in the art given the teachings of this specification.

In the target cassette, this "inducible promoter" is operatively linked and controls expression of the regulatory nucleic acid sequence or gene. The high level expression of the gene operates to decrease the accumulation of the ethylene-inducible signal protein, e.g., EIN2 or EIN3, and thereby modulates ethylene sensitivity, as identified below. The inducible promoter of the target cassette is induced by a chemical inducing composition or inducer which, when in contact with the ligand binding domain of the activation cassette, activates the response element of the minimal promoter.

F. The Nucleic Acid Sequence Encoding a Selected Regulatory Protein

The nucleic acid sequence useful in this system encodes a selected regulatory protein that modifies ethylene sensitivity or ethylene production in the plant by regulating the turnover of an ethylene inducible signal protein, such as EIN2 or EIN3. Such a nucleic acid sequence includes, in certain embodiments, the EIN3 binding F-box proteins, EBF1 and EBF2. In another embodiment, the selected regulatory proteins are the F-box proteins ETP1 and ETP 2 (Qiao et al, 2008, cited above).

An example of such an ETP1 nucleic acid sequence is identified in SEQ ID NO: 1 from nucleotides 2557 to 3804 (see also GENBANK Acc. No. NM_112874). An example of such an ETP2 nucleic acid sequence is identified as SEQ ID NO: 2 from nucleotides 2551 to 3717 (see GENBANK Acc. No. NM_112777). An example of an EBF1 nucleic acid sequence is published as GENBANK Ace. No. NM_128106. An example of an EBF2 nucleic acid sequence is published as GENBANK Acc No. NM_122444. These sequences are incorporated herein by reference.

In addition to the use of wildtype, or naturally occurring plant regulatory genes, the gene expression system may also employ certain nucleic acid sequences that contain mutations useful in these gene sequences and encoded proteins.

In one embodiment of the invention described herein, the wildtype regulatory gene that controls turnover of the selected signal protein EIN2 or EIN3 for a particular plant is used in the gene expression system and in the methods described herein to control or modulate ethylene sensitivity in the plant by inhibiting accumulation of the signal protein in the presence of ethylene. In another embodiment, mutated versions of the wildtype protein that mediates ethylene sensitivity or ethylene production in the plant cell are employed. In still further embodiments, a wildtype or mutated variant of a gene that encodes a protein that modifies ethylene sensitivity or ethylene production in one species of plant cell by inhibiting accumulation of the signal protein in the presence of ethylene is used in another species of plant cell, where such use is desirable, e.g., to eliminate potential RNA silencing.

G. Optional Components

Optional components found in the cassettes of the gene expression system include termination control regions. Such terminator or polyadenylation sequences may also be employed in the activation and target cassettes in certain embodiments of this invention. Such regions are derived from various genes native to the preferred hosts. In one embodiment of the invention, the termination control region comprises or is derived from a synthetic polyadenylation signal, nopaline synthase (nos), cauliflower mosaic virus (CaMV), octopine synthase (ocs), *Agrobacterium*, viral, and plant terminator sequences, or the like.

Selectable markers can include an antibiotic or chemical resistance gene that is able to be selected for based upon its effect, i.e., resistance to an antibiotic, resistance to a herbicide, colorimetric markers, enzymes, fluorescent markers, and the like. Examples of selectable marker genes known and used in the art include: genes providing resistance to ampicillin, streptomycin, gentamycin, kanamycin, hygromycin, actinonin (PDF1 gene), bialaphos herbicide, glyphosate herbicide, sulfonamide, mannose and the like; and genes that are used as phenotypic markers, i.e., anthocyanin regulatory genes, isopentanyl transferase gene, GUS and luciferase.

Other regulatory sequences, such as nucleotide sequences that function as spacer sequences in the plasmids, and other minor regulatory sequences, enzyme cleavage sites, and the like, may also be found in the cassettes or in the plasmids that contain the cassettes for transformation into a plant cell according to certain embodiments described herein.

The appropriate termination sequences, selectable markers, and other conventional plasmid regulatory sequences may be readily selected by one of skill in the art from among numerous such sequences well known to those of skill in the art and well described in the literature given the teachings herein.

H. Inducing Compositions/Inducers Useful for the Gene Expression System

When the gene expression system is expressed in the plant, modulation of the expression of the selected regulatory protein, e.g., overexpression of that protein, is employed to selectively modulate ethylene sensitivity in the plant cell based upon the control by the regulatory protein on the expression and accumulation of the selected signal protein. Overexpression of the regulatory protein causes a decrease in expression of the signal protein. In the presence of ethylene, the overexpression of the regulatory protein is at a high level sufficient to overcome the normal influence of ethylene on the signal protein (i.e., increased expression). The degree of overexpression of the regulatory protein is controllable by the timing, duration and amount of an inducing composition applied to the plant. In one embodiment, the inducing composition is a chemical that is placed in contact with the cells of the plant. In another embodiment, the inducing composition is a chemical that is absorbed by the cells of the plant. In yet another embodiment, the inducing composition is a chemical that is translocated within the plant cells. The inducing composition is also a ligand that is highly specific for the EcR LBD of the activation cassette. Binding of the inducing composition or ligand to the LBD of the activation cassette results in induction of the inducible promoter of the target cassette and expression of the nucleic acid sequence encoding the selected regulatory protein. Thus this system modulates ethylene sensitivity in the plant by decreasing or suppressing expression of the signal protein. The inducing composition also is characterized by low toxicity to the plant cells, tissues, and organs. The inducing composition also has the ability to be rapidly depleted from the plant to "turn off" the modulation of ethylene sensitivity, and allow efficient control of the modulation, as described in more detail below.

Among such effective inducing compositions are ligands that preferentially bind to the ecdysone ligand binding domain. In certain embodiments, these ligands include diacylhydrazine compounds, including the commercially available tebufenozide (Dow AgroSciences), methoxyfenozide (Dow AgroSciences), halofenozide (Dow AgroSciences), and chromafenozide (Nippon Kayaku) (see International Patent Publication No. WO 96/027673 and U.S. Pat. No. 5,530,028). Other useful inducers are non-steroidal ligands including the dibenzoylhydrazine derivatives described in U.S. Pat. No. 6,258,603. Still other useful inducers are the 4-tetrahydroquinoline derivatives described in detail in US Patent Application Publication No. US 2005/0228016. A number of additional suitable compounds, such as 1-Aroyl-4-(arylamino)-1,2,3,4-tetrahydroquinoline (THQ), are listed in Kumar et al, J. Biol. Chem. 2004, 279(26):27211-8; Hormann et al, J. Comput Aided Mol. Res 2003, 17(2-4):135-53; Tice et al, Bioorg Med Chem Left 2003, 13(11:1883-6; and Tice et al, 2003 Bioorg Med Chem Lett. 2003, 13(3):475-8.

Thus, the gene expression system is induced or "turned on" by a chemical inducing composition or inducer which, when in contact with the ligand binding domain of the activation cassette, activates the response element of the minimal promoter and thus turns on expression of the regulatory nucleic acid sequence or gene that in turn suppresses expression of the signal protein EIN2 or EIN3, making the plant ethylene insensitive. This gene expression system also provides the means for externally expressing the regulatory genes at sufficiently high levels to overcome the effects of ethylene on the expression of the signal proteins.

II. THE TRANSGENIC PLANT, PLANT CELL, TISSUE OR ORGAN

As described above, the gene expression system is designed for integration into a plant, plant cell or other tissue or organ of a plant. Optionally, such integration may also be transient. However, in certain embodiments of this invention stable integration into the chromosomes of the plant is desired.

In one embodiment, a transgenic plant cell is designed that expresses a gene expression system as described above and in which ethylene sensitivity is temporally and reversibly controlled. Such a plant cell, in one embodiment, is a cell into which the activation cassette and target cassette of the gene expression system are transfected or transformed. In one embodiment, wherein the activation and target cassettes are on the same plasmid, this plasmid is transfected or transformed into plant cells. In another embodiment, where the activation and target cassettes are on separate plasmids, both plasmids are separately or together transfected or transformed into the same plant cell. Alternatively, each of the two separate plasmids is transfected or transformed into a different cell of the same plant. In still an alternative embodiment, each of the two plasmids is transformed separately into a different plant, and each plant carrying a single plasmid is sexually crossed to produce a hybrid containing both plasmids, thus providing a functional inducible system.

Transfection involves introducing the exogenous or heterologous RNA or DNA inside the cell, so as to effect a phenotypic change. Transformation refers to the transfer and integration of a nucleic acid fragment into the chromosomal DNA of the plant cell, resulting in genetically stable inheritance. Thus, plant cells containing the transformed nucleic acid fragments are referred to as "transgenic" or "recombinant" or "transformed" organisms. Thus, progeny of the initially transformed or transfected plant cells also have the cassettes transiently or stably integrated into their chromosomes.

A. Transformation

The transformation of the plant cell involves producing vectors or plasmids that comprise only the activation cassette, only the target cassette, or both cassettes. See, the examples of FIGS. 1, 2, 3A-3I, and 4A-4I. Suitable vector and plant combinations are readily apparent to those skilled in the art and can be found, for example, in Maliga et al, 1994 Methods in Plant Molecular Biology: A Laboratory Manual, Cold Spring Harbor, N.Y.

For example, a suitable "vector" is any means for the cloning of and/or transfer of a nucleic acid into a plant cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication, i.e., capable of replication under its own control. Vectors useful to transform plant cells with the gene expression system include both viral and nonviral means for introducing the nucleic acid into a cell. A large number of vectors known in the art may be used to manipulate nucleic acids, incorporate response elements and promoters into genes, etc. Possible vectors include, for example, plasmids or modified plant viruses including, for example bacteriophages such as lambda derivatives, or plasmids such as pBR322 or pUC plasmid derivatives, or the Bluescript vector. Conventional means of ligating the appropriate DNA fragments into a chosen vector that has complementary cohesive termini or enzymatically modifying a suitable insertion site by ligating nucleotide sequences (linkers) into the DNA termini are known. Any viral or non-viral vector that can be used to transform plant cells is useful for this purpose. Non-viral vectors include plasmids, liposomes, electrically charged lipids (cytofectins), DNA-protein complexes, and biopolymers. In addition to the cassettes of the gene expression system, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Vectors or plasmids may be introduced into the desired plant cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963 967; Wu and Wu, 1988, J. Biol. Chem. 263:14621 14624; and Hartmut et al., U.S. Pat. No. 5,354,844). Alternatively, the use of cationic lipids may promote encapsulation of negatively charged nucleic acids, and also promote fusion with negatively charged cell membranes (Feigner and Ringold, 1989 Science 337:387 388). Particularly useful lipid compounds and compositions for transfer of nucleic acids are described in U.S. Pat. Nos. 6,172,048, 6,107,286, and 5,459,127. Other molecules are also useful for facilitating transfection of a nucleic acid, such as a cationic oligopeptide or cationic polymer (e.g., U.S. Pat. No. 5,856,435), or peptides derived from DNA binding proteins (e.g., U.S. Pat. No. 6,200,956). It is also possible to introduce a vector as a naked DNA plasmid (see U.S. Pat. Nos. 5,693,622, 5,589,466 and 5,580,859). Receptor-mediated DNA delivery approaches can also be used to effect transformation of the gene expression cassettes into the plant cell. Transformation of plants may be accomplished, e.g., using *Agrobacterium*-mediated leaf disc transformation methods of Horsch et al, 1988 Leaf Disc Transformation: Plant Molecular Biology Manual) or other methods known in the art.

B. Propagation and Screening

Thus, after transforming at least one cell in the plant with the gene expression system described above (in a single plasmid or as multiple transformed plasmids, each containing a different cassette), a method for producing a transgenic plant, plant tissue or plant organ further includes propagating a plant, or plant hybrid as described above, from the transformed plant cell or plant under conditions typical for the selected plant. The plants are then screened to select the plants (cells, tissues, organs) comprising or demonstrating the phenotypic traits of a transformed plant cell. For example, subsequent screening of the resulting plants or cells, tissues and organs thereof, is conducted to determine whether the plant contains the desired integrated nucleic acid sequences of the gene expression cassettes are also known to those of skill in the art. For example, cells which have stably integrated the introduced DNA into their chromosomes can be selected by the use of one or more reporter genes or markers in the plasmids. In the examples below, kanamycin, actinonin or bialaphos is employed for this purpose.

A plant (tissue or organ) that has successfully integrated the expression system demonstrates rapid ethylene insensitivity when the plant is contacted with an inducing composition as described above. Any plant (including plant cell, tissue, or organ) is susceptible to such transformation and thus recombinant plants may be bred by conventional means. Plants that are particularly desirable for transformation with the gene expression system and thus susceptible to modulation of their ethylene sensitivities include dicotyledons, monocotyledons, decorative, flowering plants as well as plants or plant parts for human or animal consumption. Without limitation, such plants include rice, maize, wheat, barley, sorghum, millet, switchgrass, miscanthus, grass, oats, tomato, potato, banana, kiwi fruit, avocado, melon, mango, cane, sugar beet, tobacco, papaya, peach, strawberry, raspberry, blackberry, blueberry, lettuce, cabbage, cauliflower, onion, broccoli, brussel sprout, cotton, canola, grape, soybean, oil seed rape, asparagus, beans, carrots, cucumbers, eggplant, melons, okra, parsnips, peanuts, peppers, pineapples, squash, sweet potatoes, rye, cantaloupes, peas, pumpkins, sunflowers, spinach, apples, cherries, cranberries, grapefruit, lemons, limes, nectarines, oranges, peaches, pears, tangelos, tangerines, lily, carnation, chrysanthemum, petunia, rose, geranium, violet, gladioli, orchid, lilac, crabapple, sweetgum, maple, poinsettia, locust, ash, poplar, linden tree and *Arabidopsis thaliana*.

Plant tissues and organs include, without limitation, vegetative tissues, e.g., roots, stems, or leaves, and reproductive tissues, such as fruits, ovules, embryos, endosperm, integument, seeds, seed coat, pollen, petal, sepal, pistils, flowers, anthers, or any embryonic tissue.

III. METHOD FOR CONTROLLING ETHYLENE SENSITIVITY

Such transgenic plants, cells, tissues, flowers, seeds or organs may be subject to a method for controlling ethylene sensitivity by using an effective amount of the inducing composition for a sufficient duration and applied at an appropriate time to inhibit the accumulation of a signal protein, such as EIN2 or EIN3, particularly when the plant cell is exposed to ethylene The inducing composition may be contacted with, absorbed by, and/or translocated within, the cells of the transgenic plant, plant cells, plant tissues or plant organs. Application techniques include, without limitation, immersing, spraying, powdering, drenching, dripping, or irrigating the plant, or soil or media in contact with the plant, with the inducer.

In the presence of the inducing composition, the response of the plant cells to ethylene is modulated by increasing the expression of the selected regulatory or turnover protein. In the examples below in which the selected protein is EPT1, the application of the inducer increases the expression of EPT1, which decreases or suppresses expression of EIN2 and inhibits its accumulation in the cell, thereby decreasing sensitivity of the plant to ethylene. This decrease in sensitivity lasts for the time during which the inducer is being applied to the plant (cell, tissue or organ), and for such time as the plant continues to metabolize the remaining inducer once active application is stopped. Further this decrease can occur in the presence of ethylene by overexpressing the regulatory protein to the extent necessary to counteract the directly competing effect of ethylene on the induction and expression of the ethylene-inducible signal protein. The response of the plant cells to ethylene is returned to wild-type, in this case, increased, after a selected time by depriving the plant of the inducer. "Control", "modulation" or "regulation" of the expression of the regulatory protein that affects expression of the signal protein and modulates ethylene sensitivity or ethylene production in the plant cells may be accomplished in several ways. In one embodiment of the method, modulation of the regulatory protein expression (including the quantitative magnitude of that expression) is controlled by the timing of application of the inducing composition to the plant. In another embodiment, the concentration of the inducing composition applied to the plant is used to control protein expression (including the quantitative magnitude of that expression) and thus ethylene sensitivity. In still a further embodiment, the modulation of the protein expression (including the quantitative magnitude of that expression) is controlled by the duration of the application of the inducing composition to the plant. Any one, two or all three of these parameters of application of the inducing composition may be varied during growth of the plant to obtain the desired result.

As one example of control through timing, the inducing composition may be applied at a selected time in the plant's growth cycle to modulate ethylene sensitivity, e.g., before or after one of the germination, fruit ripening, or flowering of the plant or in response to an environmental condition (e.g., before or after the plant is exposed to a stress factor, such as a pathogen or drought). In another embodiment, the inducing composition is applied at multiple times in the growth cycle of the plant. In still other embodiments, the application of the inducing composition is ceased at selected times in order to control ethylene sensitivity. The desired timing of application may be selected and varied depending upon the type of plant being treated, the potency of the inducing composition, and its possible cytotoxic effects on the plant.

As one example of control through inducing composition concentration, the inducing composition is applied to the plant in a selected concentration based upon identity of the inducing composition, the type of plant, the timing of the application (i.e., whether the plant is or has been exposed to ethylene at the time of application of the inducing composition), the size or age of the plant (e.g., seedling or mature plant), and the circumstances of application (e.g., in the field or in tissue cultures, pots or other laboratory or growing containers). In one embodiment, the inducing composition is applied at a concentration of at least 0.01 µM per plant, e.g., in tissue culture. In another embodiment, the inducing composition is applied at a concentration of at least 0.1 µM per plant. In another embodiment, the inducing composition is applied at a concentration of at least 1 µM per plant. In another embodiment, the inducing composition is applied at a concentration of at least 10 µM per plant. In another embodiment, the inducing composition is applied at a concentration of at least 20 µM per plant. In another embodiment, the inducing composition is applied at a concentration of at least 50 µM per plant. In another embodiment, the inducing composition is applied at a concentration of at least 100 µM per plant. In another embodiment, the inducing composition is applied at a concentration of at least 200 µM per plant. In another embodiment, the inducing composition is applied at a concentration of at least 500 µM per plant. In another embodiment, the inducing composition is applied at a concentration of at least 700 µM per plant. In another embodiment, the inducing composition is applied at a concentration of at least 1 mM per plant. In another embodiment, the inducing composition is applied at a concentration of at least 3 mM per plant. In another embodiment, the inducing composition is applied at a concentration of at least 5 mM per plant. In still other embodiments, the concentration is selected from among any fractional concentration between 0.01 µM to at least 5 mM.

The third method of controlling modulation of the protein mediating ethylene sensitivity or ethylene production in the plant involves varying the duration of application of the inducing composition. For example, the duration of application of the inducing composition to the plant may range from an application time of at least 10 minutes for at least 2 weeks or more, depending upon the effect desired, the potency of the inducer and the likelihood of undesirable cytotoxic effects. If desired, the application of the inducing composition may be given over a period of several days. In some embodiments, the application of the inducing composition may be given over a period of several weeks. In one embodiment, the above-noted concentrations are generally applied to the plant(s) for at least 10 minutes. In another embodiment, the above-noted concentrations are applied to the plant(s) for at least 20 minutes to decrease accumulation of the signal protein when in the absence of ethylene. In another embodiment, when the plant cell is exposed to ethylene which normally increases expression of the signal protein, the inducing composition is applied for at least 30 minutes. In another embodiment, the inducing composition is applied for at least 1 hour. In another embodiment, the inducing composition is applied for at least 2 hours. In another embodiment, the inducing composition is applied for at least 5 hours. In another embodiment, the inducing composition is applied for at least 12 hours. In another embodiment, the inducing composition is applied for at least 1 day. In another embodiment, the inducing composition is applied for at least 2 days. In some embodiments, it may be necessary or desirable to apply the inducing composition for at least or up to 2 weeks. In one embodiment, the application timing and concentration are selected by the person of skill in the art to inhibit accumulation of the signal protein when the plant is in the absence of ethylene, e.g., before the plant undergoes stress or in the anticipation of stressful conditions for the plant. In another embodiment, the application timing and concentration are selected by the person of skill in the art to inhibit accumulation of the signal protein when the plant is in the presence of ethylene, e.g., while the plant is undergoing stress.

For example, one protocol involves applying greater than 10 µM per plant for about 10 to 240 minutes to decrease or inhibit the accumulation of the signal protein when the plant is in the absence of ethylene. For example, one protocol involves applying greater than 50 µM per plant for about 5 hours to 2 days to overcome the competing reaction of ethylene on expression and accumulation of the signal protein in the plant cell. For example, see Example 7 below, which demonstrates how the concentration of the inducer modulates the degree of ethylene sensitivity shown by the plant. In a manner similar to the control by timing of application, the concentration of the inducing composition may be used to respond to the changing requirements of the plant at different growth stages or in response to changing environmental conditions.

The composition and physical chemical properties of the various inducers detailed previously may affect the application time and concentration necessary to obtain the desired biological effect. Given the teachings provided herein, the concentration, timing and duration of application as well as the inducing composition itself can be selected by an experienced grower without undue experimentation.

In general, the time between ceasing application of inducer to reversal of the plants' response to the inducer is about 2 or more days depending upon the size of the plant, the method of application, and the amount of inducer applied.

The following examples detail how increasing the expression of ETP1, ETP2, and/or decreasing the expression of EIN2, in a plant makes the plant less sensitive to ethylene. However, one of skill in the art would readily appreciate that in a similar fashion, increasing the expression of other regulatory proteins, e.g., EBF1, EBF2, and/or decreasing the expression of another ethylene-induced signal protein, e.g., EIN3, in a plant makes the plant less sensitive to ethylene. The response of the plant cells to ethylene is reversed, in this case, increased, after a selected time by depriving the plant of the inducer. This allows the plants to continue to develop, mature and ripen normally once the induction is removed.

Application of the inducer to a plant stably transformed with the gene expression system described herein permits control of one or more characteristics of plant growth sensitive to ethylene, such as, for example, senescence, fruit ripening, germination, pathogen resistance, leaf abscission, flower abscission, bud abscission, boll abscission, fruit abscission and flowering, as well as the plant's response to stress, such as caused by conditions of drought, heat, population density and salinity, among others.

The methods described herein also can be employed more specifically as methods for increasing a plant's resistance and/or tolerance to disease by increasing the ethylene insensitivity of the plant. Alternatively, the method can be applied to delay ripening or flowering of a plant, tissue or organ, e.g., for purposes of storage or transportation, by increasing the ethylene insensitivity of the plant. In still another embodiment, the method of using the transformed plants described herein with the suitably timed application of the inducer composition enables the treatment of plants undergoing undesirable growing conditions, such as drought or excessive heat, by applying the inducing composition to decrease sensitivity to ethylene and allow the plant to more readily tolerate the environmental conditions. One of skill in the art of plant propagation and growth can readily select instances in which the transformed plants and the method of induction of expression of the nucleic acid sequences described above will provide benefits based on the teachings of this specification.

Therefore, timing, duration or concentration of application of the inducer may be altered during growth of the plant using the methods described herein to control the ethylene sensitivity and thus the growth characteristics of the plant with considerable precision.

IV. THE EXAMPLES

The following examples demonstrate use of an above-described gene expression system, which comprises an activation cassette comprising, under control of a constitutive G10-90 promoter and in operative association therewith, (a) a GAL4 DBD that recognizes a response element comprising five copies of GAL4 response element; (b) an ecdysone receptor LBD comprising domains D, E and F; and (c) a VP16 AD which is activated in the presence of an inducing composition. The target cassette comprises an inducible promoter comprising, in operative association, the five copies of the GAL 4 response element located upstream of the minimal 35S promoter responsive to activation of the VP16 AD, the inducible promoter controlling expression of (e) a nucleic acid sequence that encodes an ETP1 protein. According to this embodiment, components of the activation cassette and the target cassette, when in the plant cell, modulate expression of the ETP1 protein and selectively decrease ethylene sensitivity in the plant cell. This protein expression is controlled by interaction with the inducing composition, which increases expression of the selected regulatory protein, which in turn decreases expression of EIN2, and decreases ethylene sensitivity in the plant cell. This modulation in protein expression is controlled by the timing, the concentration, and the duration of the application of the inducing composition.

More specifically, the exemplified gene expression system contains an activation cassette and target cassette present on a single plasmid, p201. This plasmid is schematically illustrated in FIG. 1. Still another exemplary plasmid p202 is illustrated in FIG. 2. The nucleic acid sequences of the gene expression cassette components of each plasmid of FIGS. 1-2 are further identified as SEQ ID NOs: 1 and 2, respectively. The nucleotide sequences of gene expression cassette components of other plasmids p1004 and p1005 discussed in the examples are disclosed in FIGS. 3A-3I and 4A-4I and in SEQ ID NOs: 3 and 4.

The following examples illustrate certain embodiments of the above-discussed compositions and methods. These examples do not limit the disclosure of the claims and specification.

Example 1

Plasmids

The gene cassette components, which are individually cloned, include for the activation cassette:
the G10-90 constitutive promoter,
the VP16 activation domain,
the GAL4 DNA binding domain, and
an ecdysone receptor ligand binding domain associated with the NOS terminator
sequence.

Similarly, the target cassette components are individually cloned, including
the inducible promoter which consists of five copies of the GAL4 response element and the minimal 35S promoter, and
the ETP1 gene (GENBANK Acc. No. NM 112874) or the ETP2 gene (GENBANK Acc. No. NM 112777) and
the 35S terminator sequence. All individual sequences are identified by nucleotide numbers in SEQ ID NO: 1 described below.

In assembling the activation cassettes, the following components are fused in two different orders to make two different activation cassettes:
VP16 AD to GAL4 LBD to EcR(DEF) of DBD (abbreviated "VGE") and
GAL4 LBD to VP16 AD to EcR(DEF) of DBD (abbreviated GVE).

It should be understood that while the plasmids below have specific choices for the above components, including the EcR LBD, the order of the components as VGE or GVE, the selection of the gene subject to the inducible promoter of the target cassette, and the plasmid backbone, all such components can be selected by one of skill in the art and the plasmids readily manipulated without undue experimentation. The following specific plasmids are exemplary only.

Thereafter, plasmid DNAs are made in pBlueScript II SK⁻ backbone (Stratagene). The SK⁻ multiple cloning sites region is replaced with a new multiple cloning site containing the recognition sites for 8 by cutting enzymes. Some of these enzymatic cleavage sites are identified in FIGS. 1, 2, 3A-3I and 4A-4I of exemplary plasmids.

Exemplary *E. coli* plasmids are prepared and sequenced to confirm the nucleotide sequence. Such plasmids contain unique enzymatic cleavage sites for addition/deletion/exchange of each component as illustrated in the FIGS. 1, 2, 3A-3I and 4A-4I. Thus, each entire construct can be transferred to any other vector of choice including a binary vector for plant transformation.

The constructs made in SK⁻ minus plasmids are transferred to binary plasmid pBIN19 (American Type Culture Collection Accession No. 37327). Since pBIN19 already has neomycin plant selectable marker gene, LB, RB and nptll selectable markers, the figures and/or sequence listing does not indicate backbone sequences, but only shows the gene expression sequences of interest, i.e., the primary components of the gene expression system, e.g., the Ec receptor and inducible ETP1 or ETP2 are cloned between the left and right borders.

The following *Agrobacterium* binary plasmids are selected for use in the production of transgenic plants:

p201 [G10-90p-VGE-NosT-5xGAL-M35S-ETP1] is used to obtain transgenic plants containing the G10-90 promoter-driven VGE receptor and inducible ETP1. The expression cassette components of p201 are illustrated in SEQ ID NO: I, namely the G10-90 constitutive promoter (nucleotide 1 to 243 of SEQ ID NO: 1), the VPI6 activation domain (nucleotide 249 to 529 of SEQ ID NO: 1), the GAL4 DNA binding domain (nucleotide 534 to 985 of SEQ ID NO: 1), and an ecdysone receptor ligand binding domain (nucleotide 990 to 1997 of SEQ ID NO: 1) associated with the NOS terminator sequence (nucleotide 2070 to 2364 of SEQ ID NO: 1), the inducible promoter which consists of five copies of the GAL4 response element (nucleotide 2391 to 2492 of SEQ ID NO: 1) and the minimal 35S promoter (nucleotide 2499 to 2554 of SEQ ID NO: 1), the ETP1 gene (nucleotide 2557 to 3804 of SEQ ID NO: 1) and the 35S terminator sequence (3828 to 4038 of SEQ ID NO: 1).

p202 [G10-90p-GVE-NosT-5xGAL-M35S-ETP2] is a plasmid used to obtain transgenic plants containing the G10-90 promoter-driven GVE receptor and inducible ETP2. See FIG. 2 and SEQ ID NO: 2. The expression cassette components of p202 are the G10-90 constitutive promoter (nucleotide 1 to 243 of SEQ ID NO: 2), the GAL4 DNA binding domain (nucleotide 276 to 716 of SEQ ID NO: 2), the VP16 activation domain (nucleotide 717-974 of SEQ ID NO: 2), and mutant the T52V mutant ecdysone receptor ligand binding domain described above (nucleotide 984 to 1991 of SEQ ID NO: 2) associated with the NOS terminator sequence (nucleotide 2064 to 2358 of SEQ ID NO: 2), the inducible promoter which consists of five copies of the GAL4 response element (nucleotide 2385 to 2486 of SEQ ID NO: 2), the minimal 35S promoter (nucleotide 2493 to 2548 of SEQ ID NO: 2), the ETP2 gene (nucleotide 2551 to 3717 of SEQ ID NO: 2) and the 35S terminator sequence (3741 to 3951 of SEQ ID NO: 2).

p1004 [G10-90p-VGE-NosT-5xGAL-M35S-ETP1 and MMVp-def-rbcS-E9t] and its components are illustrated in SEQ ID NO: 3, and a map and sequence of the components shown in FIGS. 3A-3I. These components are the G10-90 constitutive promoter (nucleotide 1 to 243 of SEQ ID NO: 3), the VP16 activation domain (nucleotide 249 to 529 of SEQ ID NO: 3), the GAL4 DNA binding domain (nucleotide 534 to 985 of SEQ ID NO: 3), and ecdysone receptor ligand binding domain (nucleotide 990 to 1997 of SEQ ID NO: 3) associated with the NOS terminator sequence (nucleotide 2070 to 2364 of SEQ ID NO: 3), the inducible promoter which consists of five copies of the GAL4 response element (nucleotide 2391 to 2492 of SEQ ID NO: 3) and the minimal 35S promoter (nucleotide 2499 to 2554 of SEQ ID NO: 3), the ETP1 gene (nucleotide 2557 to 3804 of SEQ ID NO: 3), the 35S terminator sequence (3828 to 4038 of SEQ ID NO: 3), the MMV promoter (nucleotide 6265 to 5629 of SEQ ID NO: 3), the P-DEF marker gene (nucleotide 5567-4746 of SEQ ID NO: 3) and the rbcS-E9 terminator (nucleotide 4719 to 4075 of SEQ ID NO: 3).

p1005 [G10-90p-GVE-NosT-5xGAL-M35S-ETP2 and MMVp-def-rbcS-E9t] and its components are illustrated in SEQ ID NO: 4, and a map and sequence of the components shown in FIGS. 4A-4I. These components are the G10-90 constitutive promoter (nucleotide 1 to 243 of SEQ ID NO: 4), the GAL4 DNA binding domain (nucleotide 276 to 716 of SEQ ID NO: 4), the VP16 activation domain (nucleotide 717 to 974 of SEQ ID NO: 4), and the ecdysone receptor ligand binding domain described above (nucleotide 984 to 1991 of SEQ ID NO: 4) associated with the NOS terminator sequence (nucleotide 2064 to 2358 of SEQ ID NO: 4), the inducible promoter which consists of five copies of the GAL4 response element (nucleotide 2385-2486 of SEQ ID NO: 4) and the minimal 35S promoter (nucleotide 2493 to 2548 of SEQ ID NO: 4), the ETP2 gene (nucleotide 2551 to 3717 of SEQ ID NO: 4), the 35S terminator sequence (3741 to 3951 of SEQ ID NO: 4), the MMV promoter (nucleotide 6178 to 5542 of SEQ ID NO: 4), the P-DEF marker gene (nucleotide 5483 to 4662 of SEQ ID NO: 4) and the rbcS-E9 terminator (nucleotide 4632 to 3988 of SEQ ID NO: 4).

Example 2

Production of Transgenic *Arabidopsis* Plants

*Arabidopsis* plants are transformed with plasmids from Example 1 with *Agrobacterium* using the standard floral dip protocol. Seed is harvested and plated onto kanamycin containing media. Transformed plants are selected for ability to grow on kanamycin and screened by PCR to confirm presence of the ETP1 or ETP2 genes. Positive transformants are selfed to produce T1 seed. Seed is grown on kanamycin containing media to identify lines homozygous for the transgenes. Homozygous plants are used to test for induction of ethylene insensitivity.

Example 3

Effect of Modulation of Ethylene Sensitivity on *Arabidopsis* Plant Growth

A triple response assay (Guzman and Ecker, 1990 cited above, modified as described below) is used to determine the modulation of ethylene sensitivity in the transformed *Arabidopsis* plants of Example 2. Wild-type, ein2-5 (an ethylene insensitive mutant control) and p1004 or p1005 *Arabidopsis* transformant seedlings are assayed. *Arabidopsis* seed is surface-sterilized and imbibed in 20 µM inducer in the dark for 4 days at 4° C. The seed is plated on 0.5× MS with 1% sucrose and 20 µM inducer with and without 20 µM ACC (the precursor of ethylene) and grown in the dark for 4-8 days at 21° C. In some experiments, 5 µM $AgNO_3$ (an inhibitor of ethylene that induces ethylene insensitivity) is added to the media as a control. The response to ethylene is scored on the last day. The transgenic plants containing the activation and target cassettes for expression of ETP1 or ETP2 in the presence of inducer demonstrate ethylene insensitivity, based on increased shoot length and/or altered root growth compared to non-induced transgenic plants grown in the presence of the ethylene precursor, ACC. It is anticipated that the results of this example will demonstrate that the gene expression system and plants transformed therewith, when treated with the selected inducing compositions to which the gene expression systems respond, permit successful modulation of ethylene sensitivity. The transgenic plants containing the activation and target cassettes for expression of ETP1 or ETP2 in the presence of inducer are anticipated to demonstrate ethylene insensitivity, based on increased root length compared to non-induced transgenic plants under the same circumstances.

Example 4

Production of Transgenic Tomato Plants and Effect of Modulation of Ethylene Sensitivity of Plant Growth Tomato cotyledon pieces are transformed using the plasmids from Example 1 by *Agrobacterium* using standard methods. Putative transformants are selected using either kanamycin or actinonin and confirmed by PCR analysis. Positive transformants are selfed twice to obtain lines homozygous for the transgenes. Homozygous plants are used to test for induction of ethylene sensitivity in a manner similar to that of Example 3.

A triple response assay (Guzman and Ecker, 1990, cited above, modified as described below) is used to determine the modulation of ethylene sensitivity in the transformed tomato plants. Seed from homozygous independent p1004 or p1005 lines are germinated in the dark on 0.5× MS medium+1% sucrose containing 20 µM ACC, the precursor to ethylene. Germination on ACC inhibits tomato seedling growth. Seed from the same lines also is germinated in the presence of 20 µM ACC plus 20 µM inducer. Seedlings are grown in the dark for 4-8 days at 21° C. The response to ethylene is scored on the last day.

The transgenic plants containing the activation and target cassettes for expression of ETP 1 or ETP2 in the presence of inducer demonstrate ethylene insensitivity, based on increased shoot length and/or altered root growth, compared to non-induced transgenic plants grown in the presence of the ethylene precursor, ACC. This example further demonstrates that the gene expression system and plants transformed therewith, when treated with the selected inducing compositions to which the gene expression systems respond, permit successful modulation of ethylene sensitivity.

Example 5

Production of Transgenic Corn Plants and Effect of Modulation of Ethylene Sensitivity on Corn Plant Growth Corn plants are transformed using the plasmids for Example 1 by microparticle bombardment. Putative transformants are selected using either actinonin or bialaphos and confirmed by PCR analysis. Positive transformants are backcrossed to inbred B73 to increase vigor. Transgenic corn plants produced as described above are tested for modulation of ethylene sensitivity. Modulation of ethylene sensitivity is determined at the molecular level by exposing plants to ACC, the precursor of ethylene, and measuring the change in induction of ethylene-induced genes. Stalk sheath tissue is excised from transgenic T0 corn plants grown in a green house and used in an in vitro bioassay. Excised tissue is treated with either water or 20 µM inducer for 2 days to induce expression of ETP1 or ETP2. Following the 2 day induction period, the tissue is treated for one day with 0, 1 or 10 µM ACC to produce ethylene and then harvested and used to prepare RNA.

Induction of an ethylene inducible gene (ACC oxidase) is measured using quantitative PCR on an Applied Biosystems 7900 HT Fast Real-Time PCR system (ABI), TaqMan Assay Kit (ABI) is used for reverse transcriptase (RT) and PCR using manufacturer recommended protocols. Corn 18s is used as an internal control to normalize expression for each sample.

Sequences for the primers and probes are as follows:

```
18s
Forward Primer  CGTCCCTGCCCTTTGTACAC   SEQ ID NO: 9

Reverse Primer  ACACTTCACCGGACCATTCAA  SEQ ID NO: 10

Probe           CCGCCCGTCGCTCCTACCG    SEQ ID NO: 11

ACC Oxidase(aco):
Forward Primer  GTTGTAGAAGGACGCGATGGA  SEQ ID NO: 5

Reverse Primer  CAGGTACAAGAGCGTCATGCA  SEQ ID NO: 6

Probe           TCCTGTTCCCGCTGGGCTGC   SEQ ID NO: 7
```

In order to determine gene expression, ACC oxidase expression in the 0 µM inducer plus 0 µM ACC control treatment is normalized for each respective corn line.

The transgenic plants containing the activation and target cassettes for expression of ETP1 or ETP2 in the presence of inducing compound demonstrate ethylene insensitivity, based on decreased expression of ACC oxidase. Using a similar approach, one of ordinary skill in the art also can measure a decrease in the induction of the ethylene inducible genes encoding either EIN2 or EIN3.

Example 6

Effect of ACC Concentration on Ethylene Insensitivity

Homozygous seed from one p1004 line or one p1005 line is germinated for 4 days and then grown on medium containing 20 µM inducer and either 5 µM $AgNO_3$ or various levels of the ethylene precursor, ACC (i.e., 1.0-20 µM). Hypocotyl and root length are measured after 10 days growth in the dark. Because ethylene induces EIN2 while induction of ETP1 and ETP2 target the EIN2 protein for turnover, it is expected that there may be some decrease in the level of insensitivity achieved at higher ACC concentrations as seen by slightly less hypocotl and root elongation. This example demonstrates that induction of ETP1 or ETP2 is able to induce ethylene insensitivity and the level of insensitivity of the plant can be modulated by the level of induction of ETP1 or ETP2.

Example 7

The Degree of Ethylene Insensitivity in Plants as a Function of Inducer Concentration Homozygous seeds from one p1004 containing or one p1005 containing line are germinated on medium containing 20 µM ACC and various levels of inducer (i.e., 0.5-20 Hypocotyl and root length are measured after 10 days growth in the dark. Because ethylene induces EIN2 while induction of ETP1 and ETP2 target the EIN2 protein for turnover, it is expected that there may be some decrease in the level of ethylene insensitivity achieved at lower concentrations of inducer as seen by slightly less hypocotl and root elongation. This example demonstrates that induction of ETP1 or ETP2 is able to induce ethylene insensitivity and the level of insensitivity of the plant can be modulated by adjusting the level of induction of ETP1 or ETP2.

Example 8

Transient Induction of Ethylene Insensitivity in Plants

To demonstrate that induced ethylene insensitive plants return to ethylene sensitive when the inducer is no longer provided, homozygous seeds from one p1004 line or p1005 line are germinated on medium containing 20 µM ACC and 10-20 µM inducer for 2, 4, 6, 8 or 14 days. After 14 days growth in the dark, hypocotyls and roots are measured to assess ethylene insensitivity. In the presence of ACC, ethylene insensitive seedlings are expected to have longer hypocotyls and roots. In the absence of inducer, the seedlings are expected to become sensitive to ethylene and exhibit stunted growth in the dark. Thus, root and hypocotyl growth of the reversed seedlings should be intermediate between the sensitive and insensitive seedlings. When the induced seedlings are removed from inducer, they are expected to return to a state of ethylene sensitivity when compared to the non-induced control seedlings. While the above examples show the use of the nucleotide sequences for ETP1 or ETP2, the specification clearly provides one of skill in the art with the ability to modulate expression of other regulatory genes, such as EBF1 and EBF2 in the same manner. The ethylene signal transduction pathway protein EIN3 is similarly induced by ethylene and targeted for turnover by EBF1 and EBF2. Thus, induction and modulation of EBF1 and EBF2 by use of methods and compositions described herein in a plant should result in a highly selective and temporary state of ethylene insensitivity that can be returned to ethylene sensitivity upon removal of the inducer.

Numerous modifications and variations of the embodiments illustrated above are included in this specification and are expected to be obvious to one of skill in the art. Such modifications and alterations to the compositions and processes described herein are believed to be encompassed in the scope of the claims appended hereto.

All documents, including patents, patent applications and publications, and non-patent publications listed or referred to above, as well as the attached figures and/or Sequence Listing, are incorporated herein by reference in their entireties to the extent they are not inconsistent with the explicit teachings of this specification. However, the citation of any reference herein should not be construed as an admission that such reference is available as "Prior Art" to the instant application.

What is claimed is:

1. A gene expression system for controllably inhibiting the accumulation in a plant cell of ethylene inducible proteins comprising:

an activation cassette comprising, under control of a constitutive G10-90 promoter and in operative association therewith, (a) a GAL 4 DNA-binding domain (DBD) that recognizes a response element comprising five copies of GAL4 response element; (b) an ecdysone receptor ligand binding domain (EcRLBD); and (c) a VP16 activation domain (AD) which is activated in the presence of an inducing composition; and a target cassette comprising (d) an inducible promoter comprising, in operative association, the five copies of the GAL 4 response element to which the DBD of (a) binds and the minimal 35 S promoter responsive to activation of the VP16 AD, the inducible promoter controlling expression of (e) a nucleic acid sequence that encodes an ETP1 or ETP2 protein;

said activation cassette and the target cassette in operative association to enable interaction, when in a plant cell, with an inducing composition, to controllably increase expression of the ETP1 or ETP2 protein to inhibit the accumulation of the EIN2 gene product in the plant in the presence of ethylene, the inhibition of said accumulation in EIN2 protein expression controllable by the timing, the concentration, and the duration of the application of the inducing composition.

2. The system according to claim 1, wherein the activation cassette and the target cassette are present on the same plasmid.

3. The system according to claim 1, wherein the activation cassette and the target cassette are present on separate plasmids.

4. The system according to claim 1, wherein the ecdysone receptor EcRLBD comprises all or a portion of an invertebrate ecdysone receptor or mutant thereof.

5. A composition comprising a transgenic plant cell, a transgenic plant tissue or organ, or a transgenic plant that stably expresses the gene expression system of claim 1.

6. A method for producing a transgenic plant comprising:
   (a) transforming at least one cell in the plant with the gene expression system of claim 1;
   (b) generating a plant from the transformed plant cell; and
   (c) selecting a plant comprising a transformed plant cell, which plant demonstrates ethylene insensitivity when the plant is contacted with an inducing composition in the presence of ethylene, the modulation controlled by the timing, the concentration, and the duration of the application of the inducing composition.

7. A method for modulating ethylene sensitivity in a plant comprising:
applying an inducing composition to the cells of a transgenic plant, the plant comprising cells that stably express the gene expression system of claim 1, the timing, concentration or duration of said inducing composition allowing overexpression of the regulatory protein to decrease or inhibit the accumulation of an ethylene inducible signal protein in a plant cell in the presence of ethylene.

8. The method according to claim 7, wherein the inducing composition is a diacylhydrazine compound.

9. The method according to claim 7, wherein the ethylene sensitivity that is controlled is selected from the group consisting of senescence, fruit ripening, stress response, germination, pathogen resistance, leaf abscission, flower abscission, bud abscission, boll abscission, fruit abscission, flowering, and responses to drought, heat, population density and salinity.

10. A gene expression system for controllably inhibiting the accumulation in a plant cell of ethylene inducible proteins comprising:
an activation cassette comprising, under control of a constitutive promoter and in operative association therewith, (a) a GAL 4 DNA-binding domain (DBD) that recognizes a selected response element; (b) an ecdysone receptor ligand binding domain (EcRLBD); and (c) a VP16 activation domain (AD) which is activated in the presence of an inducing composition; and
a target cassette comprising (d) an inducible promoter comprising, in operative association, a response element to which the DBD of (a) binds and a minimal promoter responsive to the AD of (c), the inducible promoter controlling expression of (e) a nucleic acid sequence that encodes an ETP1 regulatory protein that upon expression operates to decrease the expression of the EIN2 gene product;
said activation cassette and the target cassette in operative association to enable interaction, when in a plant cell, with an inducing composition, to controllably increase expression of the regulatory protein to inhibit the accumulation of the EIN2 gene product in the plant in the presence of ethylene, the inhibition of said accumulation in EIN2 protein expression controllable by the timing, the concentration, and the duration of the application of the inducing composition.

11. A method for modulating ethylene sensitivity in a plant comprising:
applying an inducing composition to the cells of a transgenic plant under stress, the plant comprising cells that stably express the gene expression system of claim 10, the timing, concentration or duration of said inducing composition allowing overexpression of the regulatory protein to decrease or inhibit the accumulation of an ethylene inducible signal protein in a plant cell in the presence of ethylene.

* * * * *